United States Patent
Howie et al.

(10) Patent No.: US 9,549,682 B2
(45) Date of Patent: Jan. 24, 2017

(54) SYSTEMS AND METHODS FOR MONITORING VITAL SIGNS BASED ON SENSED CHANGES IN A TARGET

(71) Applicant: Life Detection Technologies, Inc., Danville, CA (US)

(72) Inventors: Eric Howie, San Jose, CA (US); Guy McIlroy, Los Gatos, CA (US); John Haggis, San Jose, CA (US); Nanci Yuan, Menlo Park, CA (US)

(73) Assignee: Life Detection Technologies, Inc., Danville, CA (US)

( * ) Notice: Subject to any disclaimer, the term of this patent is extended or adjusted under 35 U.S.C. 154(b) by 0 days.

(21) Appl. No.: 14/528,812

(22) Filed: Oct. 30, 2014

(65) Prior Publication Data
US 2015/0057557 A1    Feb. 26, 2015

Related U.S. Application Data

(63) Continuation-in-part of application No. 13/841,959, filed on Mar. 15, 2013, now Pat. No. 9,035,778.
(Continued)

(51) Int. Cl.
*A61N 5/04* (2006.01)
*A61B 5/04* (2006.01)
(Continued)

(52) U.S. Cl.
CPC ......... *A61B 5/04018* (2013.01); *A61B 5/0402* (2013.01); *A61B 5/7203* (2013.01);
(Continued)

(58) Field of Classification Search
CPC .... H04W 52/0254; A61B 5/1126; A61B 5/05; A61B 2562/0214
See application file for complete search history.

(56) References Cited

U.S. PATENT DOCUMENTS 4,182,315 A * 1/1980 Vas et al. ............... 600/500
4,788,869 A * 12/1988 Li ........................... 73/861.71
(Continued)

FOREIGN PATENT DOCUMENTS

FR        2923150         5/2009
WO     WO-03048789      6/2003

OTHER PUBLICATIONS

"Heartfelt™ Infant Vitals & Video Monitoring System," Retrieved from the Internet: <URL: http://www.technophysics.com/technology/heartfelt_baby_monitor>, 4 pages (2012).
(Continued)

*Primary Examiner* — Robert N Wieland
(74) *Attorney, Agent, or Firm* — Dorr LLP

(57) ABSTRACT

Methods and systems for monitoring the well-being of a target are disclosed. In a method embodiment, data representing a signal is received by a computer system. The signal may be generated at least in part by one or more sensors in response to the detection of a change in an electrical field, electric potential, capacitance, and/or dielectric constant of a target spaced apart from the one or more sensors. The method may further include identifying, using the computer system and based at least in part on the data electronically received by the computer system, a recurring pattern in the received data. The method may also include determining, using the computer system and based at least in part on the received data, whether a deviation from the recurring pattern transgresses a threshold. The deviation may comprise a subset of the data electronically received by the computer system.

20 Claims, 17 Drawing Sheets

Related U.S. Application Data

(60) Provisional application No. 61/693,194, filed on Aug. 24, 2012.

(51) Int. Cl.
| | |
|---|---|
| *G01N 27/22* | (2006.01) |
| *G06F 19/00* | (2011.01) |
| *A61B 5/0402* | (2006.01) |
| *A61B 5/00* | (2006.01) |

(52) U.S. Cl.
CPC ............ *A61B 5/746* (2013.01); *G01N 27/22* (2013.01); *G06F 19/3431* (2013.01)

(56) References Cited

U.S. PATENT DOCUMENTS

| | | | |
|---|---|---|---|
| 6,679,830 | B2 | 1/2004 | Kolarovic et al. |
| 7,173,525 | B2 | 2/2007 | Albert |
| 7,383,071 | B1 | 6/2008 | Russell et al. |
| 7,445,605 | B2 | 11/2008 | Overall et al. |
| 7,885,700 | B2 | 2/2011 | Clark et al. |
| 8,057,388 | B1 | 11/2011 | Russell et al. |
| 2002/0013538 | A1 | 1/2002 | Teller |
| 2004/0100376 | A1 | 5/2004 | Lye et al. |
| 2004/0181703 | A1* | 9/2004 | Lilja et al. ............... 713/324 |
| 2004/0260346 | A1 | 12/2004 | Overall et al. |
| 2006/0154642 | A1 | 7/2006 | Scannell |
| 2008/0007445 | A1 | 1/2008 | Leach et al. |
| 2009/0048500 | A1 | 2/2009 | Corn |
| 2009/0240160 | A1 | 9/2009 | Thompson et al. |
| 2009/0318779 | A1 | 12/2009 | Tran |
| 2013/0267791 | A1 | 10/2013 | Halperin et al. |

OTHER PUBLICATIONS

"Non-Contact Monitor for Infants at Risk," SBIR/STTR.Award, Retrieved from the Internet: <URL: http//www.sbir.gov/sbirsearch/detail/156740>, 2 pages (2012).

"PREE Corporation's Heartfelt Infant Vitals and Video Monitoring System is Now in Pre-Sales," PREE Corporation Press Release, retrieved from the Internet: <URL: http://vvww.businesswire.com/news/home/20120215006285/en/PREE-Corporations-Heartfelt-Infant-Vitals-Video-Monitoring>, 1 page (Feb. 15, 2012).

"Standards for assessing, measuring and monitoring vital signs in infants, children and young people," Royal College of Nursing, retrieved from the Internet: <URL: http://www.rcn.org.uk/__data/assets/pdf_file/0004/114484/003196.pdf>, 16 pages (2011).

Beardsmore-Rust, S. T., "Remote applications of electric potential sensors in electrically unshielded environments," PhD. Thesis, University of Sussex. retrieved from the Internet: <URL: http://sro.sussex.ac.uk/2407/1/Beardsrnore-Rust%2C_Sam.pdf>, 185 pages (Apr. 2010).

Buckley, P., "Plessey EPIC sensor makes a heart monitor in a wristwatch," EE Times Europe, retrieved from the Internet: <URL:http://www.eetimes.com/electronics-news/4372353/Piessey-reveals-EPIC-sensor-technoloqy-to-create-a-heart-monitor-in-a-wristwatch>, 2 pages (May 6, 2012).

Connor, S. et al., "EPIC: A New Epoch in Electric Potential Sensing," retrieved from the Internet: <URL: http://www.sensorsmag.com/sensors/electric-magnetic/epic-a-new-epoch-electric-potential-sensing-8961 >, 4 pages (2011).

Connor, S., "EPIC—Introducing Plessey's multi award winning EPIC Sensor and its many applications," retrieved from the Internet: <URL:http://www.plesseysemiconductors.com/products/epic/technical/>, 5 pages (2012).

German-Sallo, Z., "Applications of Wavelet Analysis in ECG Signal Processing," PhD. Thesis, Technical University of Cluj-Napoca, 11 pages (2005).

German-Sallo, Z., "Processing of ECG Signals Using Wavelet Analysis," Acta Electrotehnica, vol. 46, No. 3, pp. 135-140 (2005).

International Application Serial No. PCT/US2013/055068, International Search Report mailed Jan. 7, 2014, 5 pages.

International Application Serial No. PCT/US2013/055068, Invitation to Pay Additional Fees and Partial Search Report mailed Oct. 13, 2013, 4 pages.

International Application Serial No. PCT/US2013/055068, Written Opinion mailed Jan. 7, 2014, 7 pages.

Saritha, C. et al., "ECG Signal Analysis Using Wavelet Transforms," Bulg. J. Phys., vol. 35, pp. 68-77 (2008).

Venkataramanan, M., "Biosensor can monitor your heartbeat from a distance," Copyright Reed Business Information Ltd., retrieved from the Internet: <URL: http://www.newscientist.com/blogs/onepercent/2011/11/sensor-monitors-your-heartbeat.html>, 6 pages (Nov. 16, 2011).

Yan, Y. et al., "Verification of a Non-Contact Vital Sign Monitoring System Using an Infant Simulator," Con. Proc. IEEE Eng. Med. Biol. Soc., 31st Annual International Conference of the IEEE EMBS, Minneapolis, MN, Sep. 2-6, 2009, pp. 4836-4839.

Yan, Y. et al., Verification of a non-contact vital sign monitoring system using an infant simulator, Con. Proc. IEEE Eng. Med. Biol. Soc., (Abstract Only), retrieved from the Internet: <URL: http://www.ncbi.nlm.nih.gov/pubmed>, 1 page (2009).

\* cited by examiner

Final output at 50mV/div and time scale of 20ms/div

Final output at 50mV/div and time scale of 200ms/div

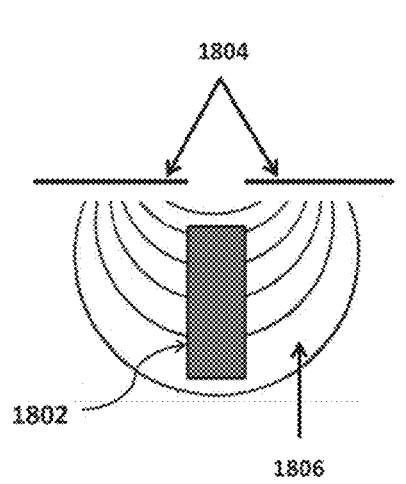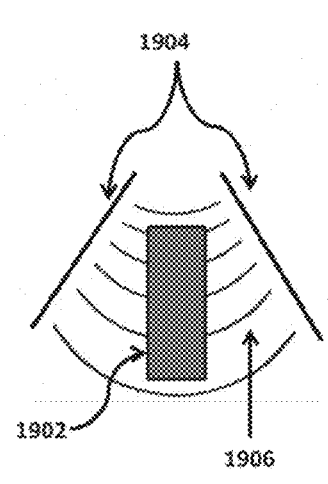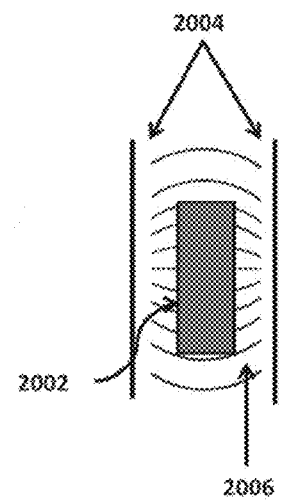
*FIG. 17A*  *FIG. 17B*  *FIG. 17C*

SYSTEMS AND METHODS FOR MONITORING VITAL SIGNS BASED ON SENSED CHANGES IN A TARGET

CROSS-REFERENCES TO RELATED APPLICATIONS

This application claims priority as a continuation-in-part of U.S. patent application Ser. No. 13/841,959, entitled "Monitoring Vital Signs Based on Sensed Changes to an Electrical Field," filed on Mar. 15, 2013, which claims priority to U.S. Provisional Patent Application No. 61/693,194, entitled "Analyzing Electrical Fields Associated With Life Forms," filed on Aug. 24, 2012, the contents of each of which are hereby incorporated by reference in their entirety.

FIELD OF INVENTION

This application relates generally to the technical field of monitoring systems, more particularly, to a monitoring system that monitors vital signs based on sensed changes in a target.

BACKGROUND

The performance of a variety of monitoring systems may be affected by where a sensor or its parts are placed relative to a target (e.g., a human such as an adult, teen, child, or baby) that is being monitored. For example, certain monitoring systems may require a sensor to be in physical contact with a target and may further require a part (e.g., a power or data cable) to be connected from a sensor to a monitoring device. Installing sensor parts in, for example, a baby crib may be contrary to expert advice to keep the baby crib free of such objects (e.g., based on the sensor parts constituting a strangulation or suffocation hazard). Alternatively, the sensor may require wireless communication between a sensor and a monitoring device, thereby introducing potentially harmful or interfering communication waves (e.g., radio frequency waves, microwave communication waves, etc.) in close proximity to the baby, another target of the monitoring system, or other electronic equipment.

Known monitoring systems require a sensor to be directly in contact with a target. For example, a traditional electrocardiogram (ECG) uses external electrodes to detect a patient's ECG signal. The external electrodes are located on the ends of cables and must be physically placed on a patient and near the patient's heart. This often necessitates the use of conductive materials that may be inconvenient to hook up and use, especially for long-term monitoring of a relatively active patient. These devices have significant limitations. For example, the patient must be physically connected to the device. If the patient wants to leave his or her bed, the device needs to be detached from, and then re-attached to the patient on his/her return, often by a highly trained staff member. The inconvenience and the delays associated with setting up such monitoring systems mean that they are not well-adapted to long-term use and, as a result, may miss detecting important but transient episodic events. These monitoring systems are also not well-suited for monitoring more active targets, for example, a baby in a crib or a person exercising on a piece of exercise equipment. Although there are monitoring systems incorporated into devices such as wristbands and armbands that are more suited to an active lifestyle, they still typically need to be directly in contact with the target, and generally provide limited information and functionality.

Accordingly, there is a need for a monitoring system that does not require a sensor to be directly in contact with a target. There is also a need for a monitoring system that can assist in the management of a target's health, fitness, sleep and diet by monitoring changes in a person's body. There is further a need for a monitoring system suitable for long-term use that can sense changes in a target and provide timely and appropriate diagnostic, prognostic and prescriptive information.

BRIEF DESCRIPTION OF DRAWINGS

Various objects, features, and advantages of the disclosed subject matter can be more fully appreciated with reference to the following detailed description of the disclosed subject matter when considered in connection with the following drawings, in which like reference numerals identify like elements. Some embodiments are illustrated by way of example and not limitation in the figures of the accompanying drawings in which:

FIGS. 17A-C show examples of different orientations of the capacitive plates of the contact-less sensor according to different embodiments.

SUMMARY

Figure 1:
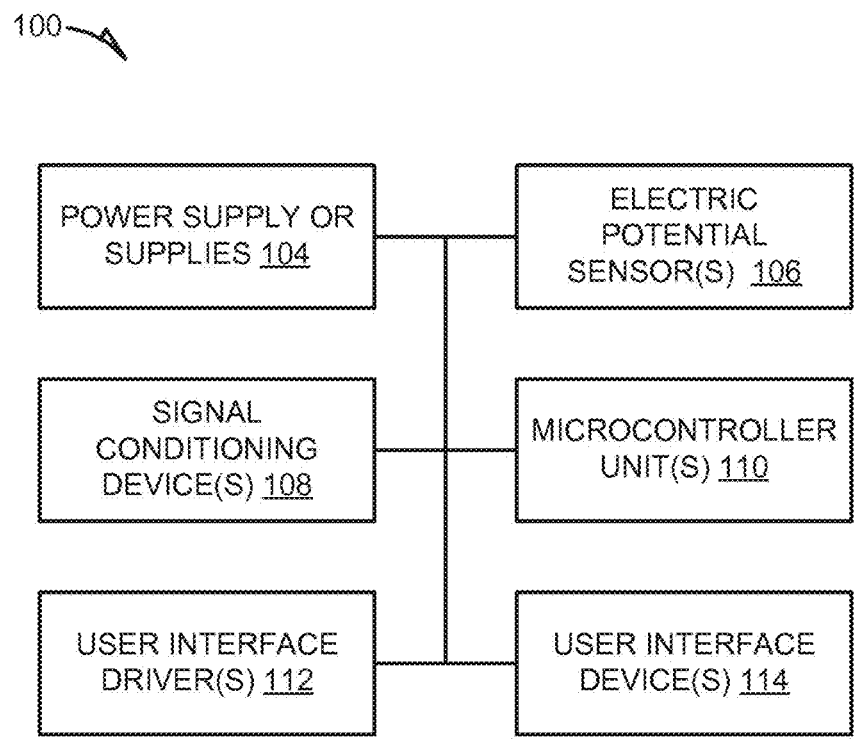
FIG. 1 is a block diagram depicting an example of an embodiment of a portion of a system capable of monitoring disturbances in electric fields.

A method of detecting a change in capacitance and/or dielectric constant in a target is disclosed herein, the method comprising: electronically receiving, by a computer system, data representing a signal generated at least in part by one or more sensors detecting a change in capacitance or dielectric constant of a target spaced apart from the one or more sensors; identifying, using the computer system and based at least in part on the data electronically received by the computer system, a recurring pattern in the data; and determining, using the computer system and based at least in part on the data electronically received by the computer system, whether a deviation from the recurring pattern transgresses a threshold, the deviation comprising a subset of the data electronically received by the computer system.

In one aspect, a system of detecting a change in capacitance and/or dielectric constant is disclosed herein, the system comprising: a memory; and one or more processors coupled to the memory, the one or more processors configured to, based on instructions contained in the memory: electronically receive data representing a signal generated at least in part by one or more sensors detecting a change in capacitance or dielectric constant of a target spaced apart from the one or more sensors, identify, based at least in part on the data electronically received, a recurring pattern in the data representing a signal, and determine, based at least in part on the data electronically received, whether a deviation from the recurring pattern transgresses a threshold, the deviation comprising a subset of the data electronically received.

In another aspect, a non-transitory machine-readable medium is disclosed herein, the non-transitory machine-readable medium storing a set of instructions that, when executed by at least one processor, causes the at least one processor to perform operations comprising: electronically receiving data representing a signal generated at least in part by one or more sensors detecting a change in capacitance or dielectric constant of a target spaced apart from the one or more sensors; identifying, based at least in part on the data electronically received, a recurring pattern in the data representing a signal; and determining, based at least in part on the data electronically received, whether a deviation from the recurring pattern transgresses a threshold, the deviation comprising a subset of the data electronically received.

Also described herein is a system comprising: one or more sensors configured to detect a change in capacitance or dielectric constant of a target spaced apart from the one or more sensors, each sensor comprising: a capacitor having two plates arranged to detect the capacitance or the dielectric constant of the target, an oscillator, coupled to the capacitor, configured to detect the change of the capacitance or the dielectric constant of the target, and a frequency-to-voltage converter, coupled to the oscillator, configured to convert the change in the capacitance or the dielectric constant of the target from a frequency to a voltage; and a computer having a memory and one or more processors coupled to the memory, the one or more processors configured to, based on instructions contained in the memory: electronically receive data representing a signal generated at least in part by the one or more sensors, identify, based at least in part on the data electronically received, a recurring pattern in the data representing a signal, and determine, based at least in part on the data electronically received, whether a deviation from the recurring pattern transgresses a threshold, the deviation comprising a subset of the data electronically received.

DETAILED DESCRIPTION

In the following description, for purposes of explanation, numerous specific details are set forth in order to provide an understanding of various embodiments of the present subject matter. It will be evident, however, to those skilled in the art that various embodiments may be practiced without these specific details. In addition, it will be understood that the examples provided below are exemplary, and that it is contemplated that there are other systems, methods and media that are within the scope of the disclosed subject matter.

The application relates to a monitoring system that does not require a sensor to be directly in contact with a target. The application also relates to a monitoring system that can assist in the management of a target's health, fitness, sleep and diet by monitoring changes in a person's body. The application further relates to a monitoring system suitable for long-term use that can sense changes in a target and provide timely and appropriate diagnostic, prognostic and prescriptive information.

In various embodiments, a method is disclosed that may be used, for example, to monitor a target. The method may include electronically receiving, by a computer system, data representing an electric field, electric potential, capacitance and/or dielectric constant signal. The signal may be generated at least in part by one or more sensors in response to the detection of a change in an electric field, electric potential, capacitance and/or dielectric constant of a target spaced apart from the one or more sensors. The method may further include identifying, using the computer system and based at least in part on the data electronically received by the computer system, a recurring pattern in the data representing an electric field, electric potential, capacitance and/or dielectric constant signal. The method may also include determining, using the computer system and based at least in part on the data electronically received by the computer system, whether a deviation from the recurring pattern transgresses a threshold. The deviation may comprise a subset of the data electronically received by the computer system.

In certain method embodiments, a pattern of disturbances in an electrical field, electric potential, capacitance, dielectric constant, and/or any other suitable type of measurement is monitored. An anomaly in the pattern of the disturbances in the electrical field, electric potential, capacitance, dielectric constant, and/or any other suitable type of measurement is detected. A correspondence between the anomaly and the threat to the well-being of the target is determined. An alarm is generated based on the determining of the correspondence.

Methods and various embodiments disclosed herein may be implemented as a computer system having one or more modules (e.g., hardware modules or software modules). Furthermore, methods and various embodiments disclosed herein may be embodied as instructions stored on a non-transitory computer-readable medium that, when executed by one or more processors, cause the one or more processors to perform the instructions.

FIG. 1 is a block diagram depicting an example embodiment of a portion of a system 100 generally capable of monitoring disturbances in electrical fields. In this example, monitoring system 100 includes multiple modules 104, 106, 108, 110, 112, and 114. Although the illustrated embodiment includes example modules 104, 106, 108, 110, 112, and 114, any suitable module(s) may be used including, for example, additional or alternative modules. As used herein, the term module generally refers to any suitable combination of hardware, software, or firmware configured to facilitate the monitoring of electrical fields, electric potential, capacitance, dielectric constant, and/or any other suitable type of measurement.

Module 104 may be, or may include, one or more power supplies that may be configured, for example, to receive power from an energy source (e.g., a battery, an alternating current (AC) line, and so on) and to supply power to various other modules of the monitoring system 100 (e.g., at specific voltages required by the other components). For example, module 104 may include a power supply having a three Volt (3V) or similar input. Furthermore, module 104 may include a buck-boost converter configured to minimized losses from input voltage to source load.

Module 106 may include one or more electric field disturbance sensors or any other suitable sensors. Certain electric field disturbance sensors or other suitable sensors may be configured, for example, to detect a fluctuation in an electric field, electric potential, capacitance, dielectric constant, and/or any other suitable type of measurement, and in response, to generate a detection signal corresponding to the detected fluctuation. As explained further below, system 100 may be capable of associating certain detected fluctuations with a particular target or with a particular movement of that target. As used herein, a target is any person or thing that is capable of disturbing an electric field, electric potential, capacitance, and/or dielectric constant. In a particular embodiment, for example, a target may be a patient undergoing a particular medical observation facilitated by system 100.

In various embodiments, the electric field disturbance sensor(s) of module 106 behave as a high impedance antenna capable of sensing electric field, electric potential, capacitance and/or dielectric constant disturbance within the vicinity, including those generated remotely from the electric field disturbance sensor(s). For example, certain electric field disturbance sensor(s) or other suitable sensors of module 106 may detect changes in electric field, electric potential, capacitance and/or dielectric constant at a distance of up to several inches, several feet, or more. In certain applications, the ability to remotely detect disturbances in electric field, electric potential, capacitance and/or dielectric constant within the vicinity may facilitate three-dimensional positional analysis of a target. As an example, whenever a human body moves, it may generate electric field, electric potential, capacitance and/or dielectric constant variations with specific characteristics that depend on the nature of the movement. Thus, heart movements, eye movements, lung movements, and limb movements, for example, may generate signals that are detectable by certain electric field disturbance sensors (s) or other suitable sensors, even if positioned remotely from the target.

Any suitable electric field disturbance sensor or other suitable sensor may be used by module 106, including those capable of detecting changes in electrical field, electric potential, capacitance and/or dielectric constant. For example, module 106 may include one or more electric field disturbance sensor(s) based on or substantially similar to the Electric Potential Integrated Circuit (EPIC) technology of Plessey Semiconductors Ltd. or to certain electric field sensors of Campbell Scientific (e.g., CS110).

In a particular embodiment, module 106 is communicatively coupled to module 108, such that a detection signal generated at module 106 may be communicated (e.g., wirelessly or by wired communication) to module 108.

Module 108 may be, or may include, one or more signal conditioning devices configured to condition or manipulate a detection signal received from module 106 into a conditioned signal that may be used, for example, to facilitate certain signal processing by system 100. Any suitable signal conditioning may be used including, for example, a combination of various types of signal conditioning. For example, the signal conditioning device(s) 108 may include an operational amplifier (op-amp) configured to amplify an analog detection signal received from the electric field disturbance sensors(s) 106. As another example, the signal conditioning device(s) 108 may include one or more filters configured to reduce noise in a detection signal received from the electric field disturbance sensors(s) of module 106, as described in more detail below. As yet another example, module 108 may be capable of receiving an analog detection signal from module 106 and performing an analog-to-digital conversion. Thus, in a particular embodiment, module 108 generally receives as an input a detection signal from module 106 and, in response, generates an output as a conditioned signal.

In a particular embodiment, module 108 is communicatively coupled to module 110, such that a conditioned signal conditioned by module 108 may be communicated (e.g., wirelessly or by wired communication) to module 110.

Module 110 may be, or may include, one or more microcontroller unit(s) configured to process signals received from one or more other modules of monitoring system 100. For example, one or more microcontroller unit(s) of module 110 may receive as an input a conditioned signal from the signal conditioning device(s) of module 108. The microcontroller unit(s) may then process the received conditioned signal, as described in more detail below.

In certain embodiments the signal generated by the one or more sensors may be caused by physiological or non-physiological changes of the target. Signals corresponding to movements of the target or parts within the target may also be generated by the sensors. When the target is a human being or an animal, signals corresponding to muscular movement, expansion or contraction of organs may also be detected. In a particular embodiment, the processing effected by module 110 may include identifying whether a conditioned signal received as a data input from module 108 corresponds to a vital sign of a target and, if so, determining whether the data indicates that the well-being of the target is threatened. As used herein, a vital sign may not only include physiological vital signs (e.g., heart movements, blood movements, lung movements, muscle movements, eye movements, brain activity, limb movements, body movements, and so on), but also non-physiological vital signs (e.g., measurements pertaining to the health of a vehicle or building). For example, the health of a building may be monitored based on sensing of termites within the walls of the building. Or the health of a vehicle (or other inanimate object) may be determined based on the sensing of a change in electric field, electric potential, capacitance, and/or dielectric constant caused by electric components of the vehicle (or object).

In a particular embodiment, module 110 is communicatively coupled to module 114, such that a communication generated at module 110 may be communicated (e.g., wirelessly or by wired communication) to module 114. For example, the microcontroller unit(s) of module 110 may be configured to communicate a result of its signal processing to one or more user interface device(s) 114 (e.g., via one or more respective user interface driver(s) 112). For example, if the microcontroller unit(s) of module 110 determine that the well-being of the target is threatened, the microcontroller unit(s) may send a communication that activates a siren or other alarm, or activates or changes a color of a light-emitting diode (LED) of the monitoring system 100.

In a particular embodiment, the user interface driver(s) may receive communications from the microcontroller unit(s) of module 110 and translate them into a format that is appropriate for the particular user interface device(s) of module 114 on which the status of the monitoring system 100 may be represented. The user interface device(s) of module 114 may include one or more sensitivity controls (e.g., dials) configured to enable a user to control the sensitivity of the electric field disturbance sensor(s) of module 106 either singularly or collectively (e.g., at particular frequencies).

In certain embodiments, the user interface device(s) of module 114 includes one or more indicators (e.g., via a display or LED) configured to indicate which ones of potentially multiple types of signals that the system 100 is currently able to detect or not able to detect with respect to a target (e.g., whether the system 100 is able to identify signals pertaining to the heart, lungs, brain, limbs, body, etc.). Thus, a user of the system 100 may be able to configure the electric field disturbance sensor(s) based on information that the user receives via the user interface device(s) 114.

Figure 2:
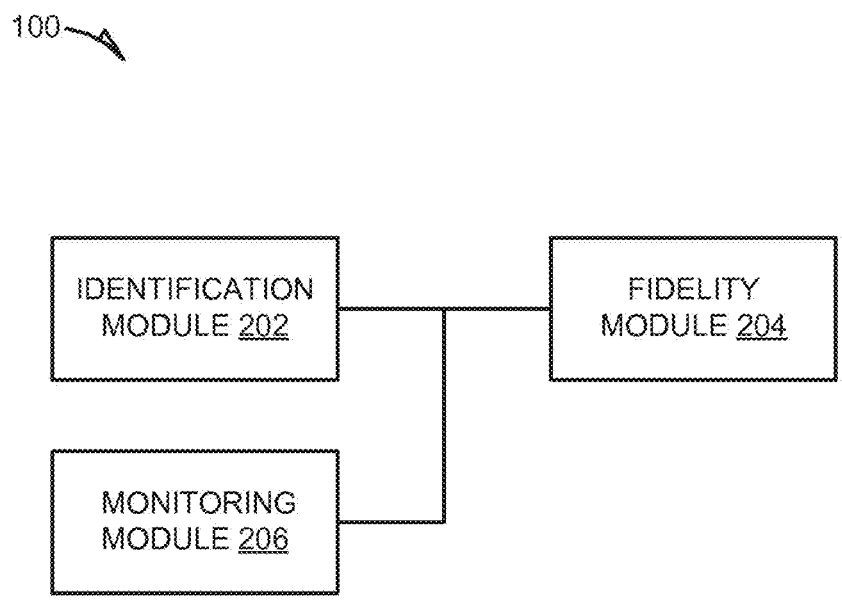
FIG. 2 is a block diagram depicting certain other example modules that may be used by the system of FIG. 1 according to a particular embodiment.

FIG. 2 is a block diagram depicting certain example modules of the system 100 of FIG. 1 according to a particular embodiment. At least a portion of certain modules may be embodied as instructions that are implemented by the microcontroller unit(s) of module 110. The system 100 may include an identification module 202 that is configured to identify, for example, vital sign electric potential signals from a process electric signal. The system 100 may include a fidelity module 204 that is configured to increase a fidelity of a candidate potential electric signal derived from a process electric potential signal (e.g., such that the candidate potential electric signal may be disambiguated from an additional candidate potential electric signal such that it may be identified as a vital sign electric potential signal), as described in more detail below.

Figure 3:
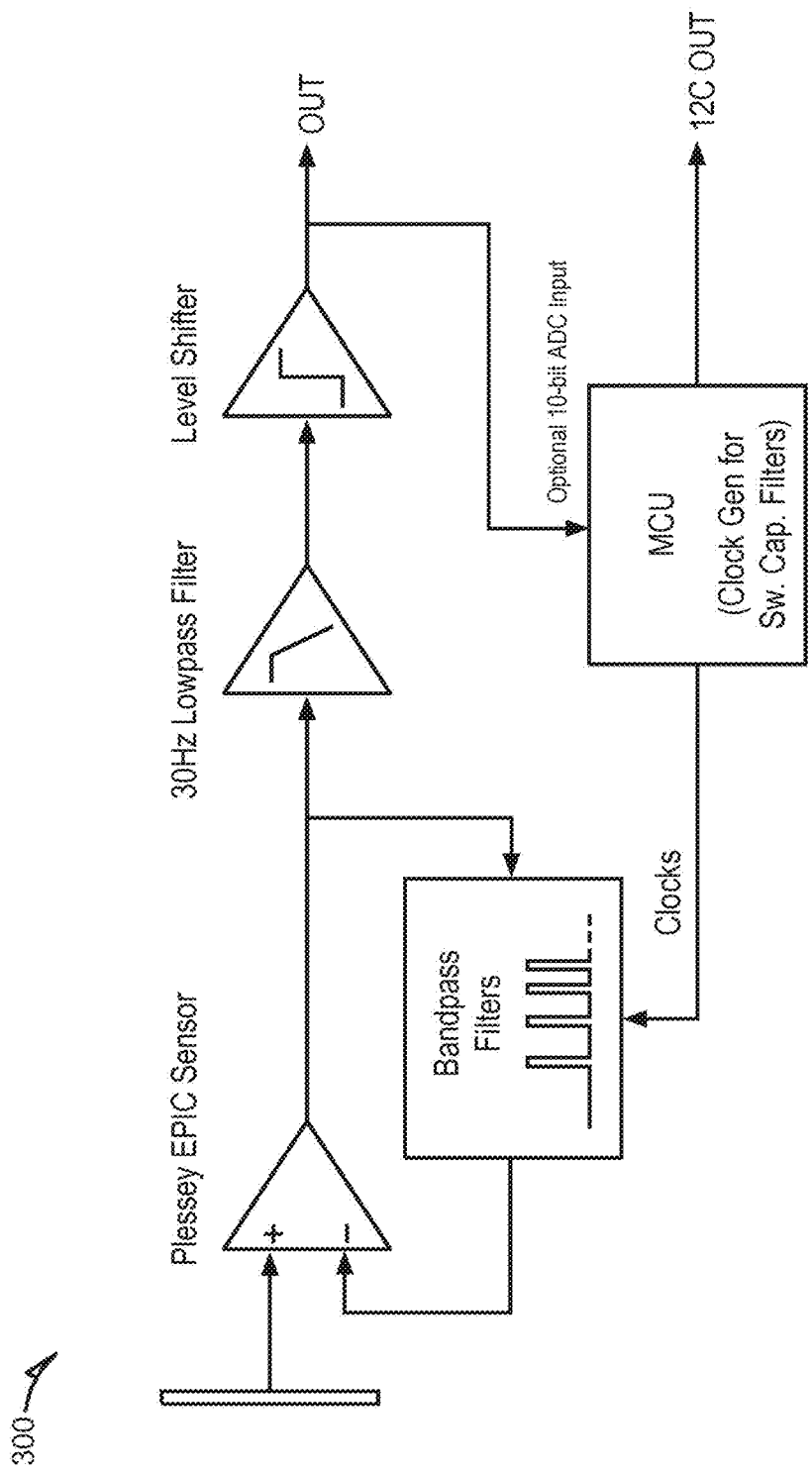
FIG. 3 is a block diagram depicting an example embodiment of a physio/motion sensor board that may be used by the system of FIG. 1 to monitor disturbances in electrical fields.

FIG. 3 is a block diagram depicting an example embodiment of a physio/motion sensor board 300 that is configured to monitor disturbances in electrical fields. The physio/motion sensor board 300 may comprise a high-impedance sensor module (e.g., a Plessey EPIC "EPS" (Electric Potential Sensor)) and certain filtering capability. The filtering capability may be configured, for example, to enhance the sensing capacity to low-level signals in the presence of high-level background electrical noise. The physio/motion sensor board 300 may also include a 30 Hz analog low-pass filter at the output and a level shifter/gain block to bring it to a 0-3.3V scale, which in certain instances may facilitate digitization by a microcontroller or DSP.

The noise suppression may work by using switched-capacitor filter chips in an inverse-notch filter (tight bandpass) configuration of 60 Hz and several of its harmonics, fed back into the negative feedback input of the high-impedance sensor. In effect, this creates a multiple-notch filter for the 60 Hz spectrum that could saturate the sensitive, high-gain amplifier at the front end.

The analog low-pass filter may be configured, for example, to filter out digital clock bleed into the signal and/or other high-frequency interference, while passing physiological signals (EKG, respiration) and very low-frequency movement.

Figure 4:
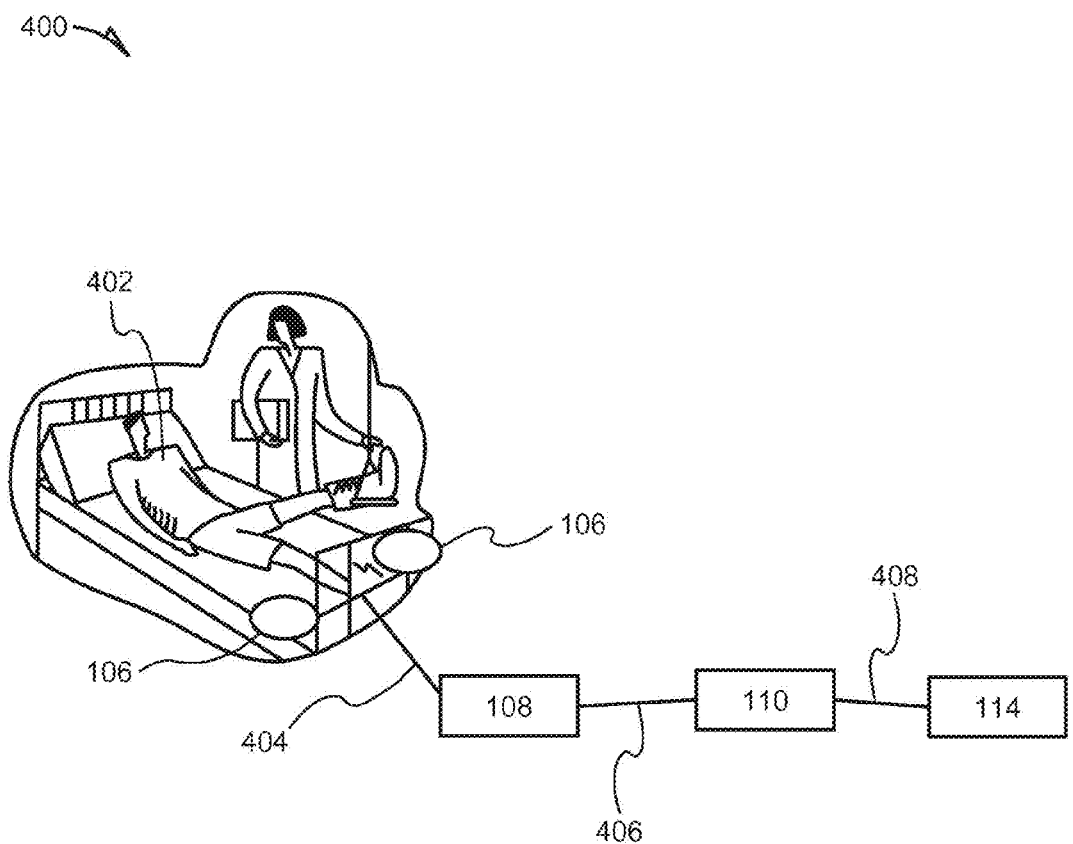
FIG. 4 is a diagram of example interactions of certain modules of FIG. 1, in which the interactions may occur during the monitoring of electric field disturbances associated with a target.

FIG. 4 is an interaction diagram of example interactions of certain modules of FIG. 1. Certain interactions may occur, for example, during the monitoring of electric field disturbances associated with a target. As shown in FIG. 4, the electric field disturbance sensor(s) 106 are in communication with the signal conditioning device(s) 108 via communication pathway 404, the signal conditioning device(s) 108 are in communication with the microcontroller unit(s) 110 via communication pathway 406, and the microcontroller unit(s) 110 are in communication with the user interface device(s) 114 via communication pathway 408.

Figure 5:
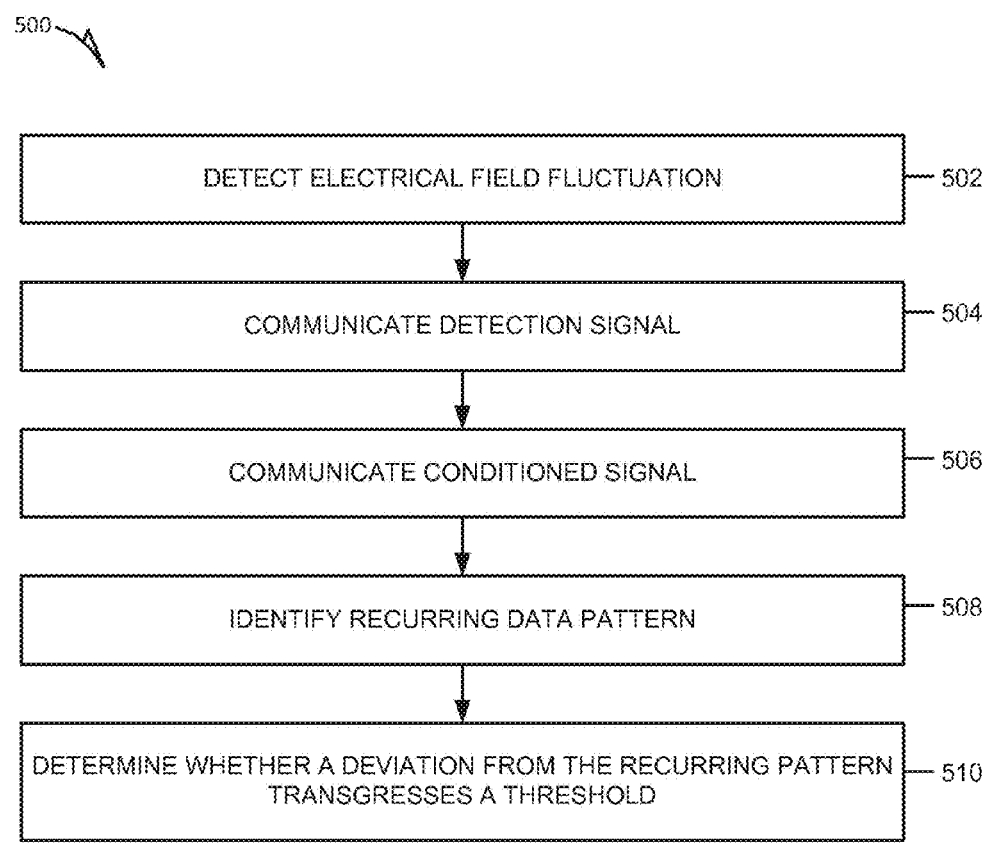
FIG. 5 is a flowchart of an example embodiment of a method of identifying electrical potential signals or electric field disturbance signals as pertaining to certain vital signs of a target.

FIG. 5 is a flowchart of an example embodiment of a method 500 for identifying electric field disturbance signals, as pertaining to certain vital signs of a target. Although FIG. 5 is described primarily in the context of detecting a fluctuation in an electric field, the invention also applies to detecting a fluctuation in electric potential, capacitance, dielectric constant, and/or any other suitable type of measurement. In various embodiments, the method 500 may be implemented by one or more of the modules of FIGS. 1-5. At operation 502, a fluctuation in an electric field is detected. As shown in FIG. 4, for example, a particular movement of a target 402 (e.g., one or more of a particular heart movement, eye movement, lung movement, limb movement) may generate signals that are detectable by one or more electric field disturbance sensor(s) 106, even if the sensor(s) are positioned remotely from the target.

In response to the detected fluctuation, a detection signal corresponding to the detected fluctuation may be communicated in operation 504. For example, module 106 may communicate the detection signal to module 108, as explained previously with reference to FIG. 1 and shown by way of example in FIG. 4 by a detection signal 404.

At operation 506, a conditioned signal may be communicated based at least in part on the detection signal communicated in step 504. As explained previously with reference to FIG. 1 and as shown in FIG. 4, for example, module 108 may receive a detection signal 404 as an input, condition the received signal, and communicate a corresponding conditioned signal 406 as an output. In particular embodiments, the signal conditioning effected at operation 506 may include filtration, amplification, conversion (e.g., inversion or analog-to-digital conversion), any combination thereof, or any other suitable signal conditioning that effects a transformation of the signal, as explained previously with reference to FIG. 1.

In certain instances, a detection signal 404 conditioned at operation 506 may include data in the 50 Hz or 60 Hz frequencies. Thus, the signal being conditioned may include disturbances in an electric field that are potentially caused at least in part by mains (or general-purpose) electricity or electric alternating-current (AC), possibly in addition to disturbances caused by the target 402. However, instead of eliminating all signals in the 50 Hz or 60 Hz frequencies from consideration as possibly pertaining to the well-being of the target 402, certain filter algorithms may be used to disambiguate signals corresponding to electric field disturbances created by the target 402 from electric field disturbances created by a standard electric power source (e.g., module 104).

In various embodiments, active filtering is performed at operation 506. Active filtering may include filtering ambient electric field disturbances from electric field disturbances caused by the target 402. Such filtering may be effected, for example, by comparing a detection signal from a first electric field disturbance sensor that is configured or positioned to capture ambient electric field disturbances in an environment of the target (but not the target itself) and a detection signal from a second electric field disturbance sensor that is configured or positioned to capture electric field disturbances of the target within the environment. In various embodiments, a single electric field disturbance sensor is used to capture both the ambient electric field disturbances and the electric field disturbances created by the target (e.g., over separate time periods). For example, a monitoring system 100 having a single electric field disturbance sensor may be placed into the environment before the target is placed in the environment for a time period (e.g., an hour). After capturing and storing data corresponding to ambient electric field disturbances in the environment, the target may be placed into the environment. Then the monitoring system 100 may use the same electric field disturbance sensor to identify electric field disturbances in the environment, which include those generated by the target. The monitoring system may then use the data pertaining to the previously identified ambient electric field disturbances to identify those electric field disturbances that are most likely created by the target. Additional processing may be used to identify particular signals as corresponding to vital signs of the target, as explained further below.

In a particular embodiment, the conditioned signal 406 is communicated at operation 506 in the form of data representing a fluctuation in an electric field that had been detected, for example, at operation 502. In certain embodiments, the data communicated at operation 506 may be computer-readable and may have a particular format suitable for processing at subsequent operations. For example, the communicated data may have a format suitable for processing by one or more microcontroller unit(s) of module 110.

At operation 508, a recurring pattern of a signal may be identified. For example, as explained previously with reference to FIG. 1, one or more microcontroller unit(s) of module 110 may perform one or more operations that facilitate identifying a recurring pattern of a signal. In certain instances, the signal analyzed for a recurring pattern may be a conditioned signal 406 in the form of computer-readable data having a particular format suitable for processing by one or more microcontroller unit(s) of module 110.

In certain embodiments, a recurring pattern may be identified at operation 508 at least in part using one or more filter algorithms. For example, a notch (50/60 Hz), low pass, high pass, any combination thereof, or other filter algorithm (s) may be used. Certain filters may be digitally implemented (e.g., by module 110 according to best practice guidelines).

In certain instances, multiple patterns may be identified at operation 508. For example, a separation analysis may be used to identify various patterns that, in certain instances, may have substantially concurrent time domain components. The various patterns may correspond to one or more respective vital signs of a target (e.g., heartbeat and breathing occurring substantially simultaneously). In a particular embodiment, the monitoring system 100 (e.g., via wavelet analysis) separates electric field disturbances pertaining to general movements of the body of a human target (as a whole) from electric field disturbances pertaining to movements of parts (e.g., heart or eye movements) of the body of the target. In various embodiments, this separation analysis may be applied to data having 50 Hz and 60 Hz components in the frequency domain; however, any suitable frequency or range of frequencies may be used. Additional detail regarding identifying multiple patterns, according to particular embodiments, is explained further below with reference to FIG. 6.

In a particular embodiment, identification of a pattern at operation 508 in multiple domains (e.g., frequency and time domains) may be achieved at least in part using wavelet transforms including, for example, Fourier Wavelet Transforms. Certain wavelet transforms may be used to decompose data into a series of functions, which may include sine and cosine functions. In particular embodiments, use of wavelet functions to identify a particular pattern may facilitate matching the characteristics of intermittent signals to the characteristics of the vital signs sought to be detected.

In certain instances, the identification of a pattern at operation 508 may include associating a particular data pattern with a respective vital sign of a target. For example, analysis of historical data may be incorporated into an algorithm for identifying a subset of data corresponding to a vital sign of a target. In certain instances, the historical data may include a property corresponding to a previously identified vital sign, such that the historical data may be used as a basis of comparison in identifying patterns associated with that vital sign. Various identified patterns may be reduced to fundamental target signals and stored for purposes of later comparison with other datasets derived from the detected electrical field disturbances caused by a target. Additional detail regarding associating a particular data pattern with a respective vital sign of a target is explained further below with reference to FIG. 6.

In particular embodiments, the recurring pattern identified at operation 508 may involve a predictable pattern that may have an expected duration but may have time domain components indicating occurrences at relatively random intervals. For example, a pattern may be identified at operation 508 as corresponding to a limb movement or eye movement that happens repeatedly but at relatively random intervals. By way of contrast, a pattern corresponding to respiration or a heartbeat, though also typically represented by a short time duration, may be identified at least in part by intervals that are relatively consistent in duration.

Certain patterns may be identified at operation 508 at least in part by their relatively short time durations (e.g., patterns corresponding to certain limb, eye, or heart movements). Certain other patterns may be identified at operation 508 at least in part by their relatively longer durations (e.g., a chest movement corresponding to respiration of a target).

Some patterns may be identified based on their recurring nature. Examples of recurring patterns may be patterns corresponding to heart beats or breathing of a target. Such patterns may be repeated substantially predictably (e.g., with a predictable gap between a first pattern and a second pattern in a series of patterns) or substantially randomly (e.g., a rapid eye movement that is repeated substantially unpredictably, with each repetition having a sufficient similarity to the other repetitions in the series. Whether a repetition is sufficiently similar to the other repetition may be determined based on a similarity (e.g., plotted measured data points corresponding to each repetition) transgressing a threshold. The recurring pattern may be identified based on a similarity between a first pattern and a second pattern in a series of patterns, such as a similarity in the length of the first pattern in comparison to the second pattern, a similarity in plotted measurements of between the first pattern and the second pattern, a range of a length of a gap between the first pattern and the second pattern, a similarity in wave forms between the first pattern and the second pattern, and so on. Examples of recurring patterns are shown by the plots of data points in FIGS. 9-12.

At operation 510, a determination may be made as to whether at least a subset of the data being analyzed deviates from a recurring pattern by an amount exceeding a particular threshold. As shown by the plot of data points in FIGS. 11-12, for example, a determination may be made that a characteristic of certain outlier data points deviate by an amount exceeding a particular threshold from a recurring pattern associated with a heart rate. In certain embodiments, the subset of data analyzed at operation 510 may be compared to historical data used at operation 508 to identify a pattern. Although in this example an analysis is performed with respect to a recurring pattern, in alternative embodiments the analysis may not involve a recurring pattern as a reference. For example, a deviation may be identified based on a property of a subset of data that is unusual in comparison to other portions of the data, such as, for example, a deviation beyond a six-sigma threshold or some other expected range.

Figure 6:
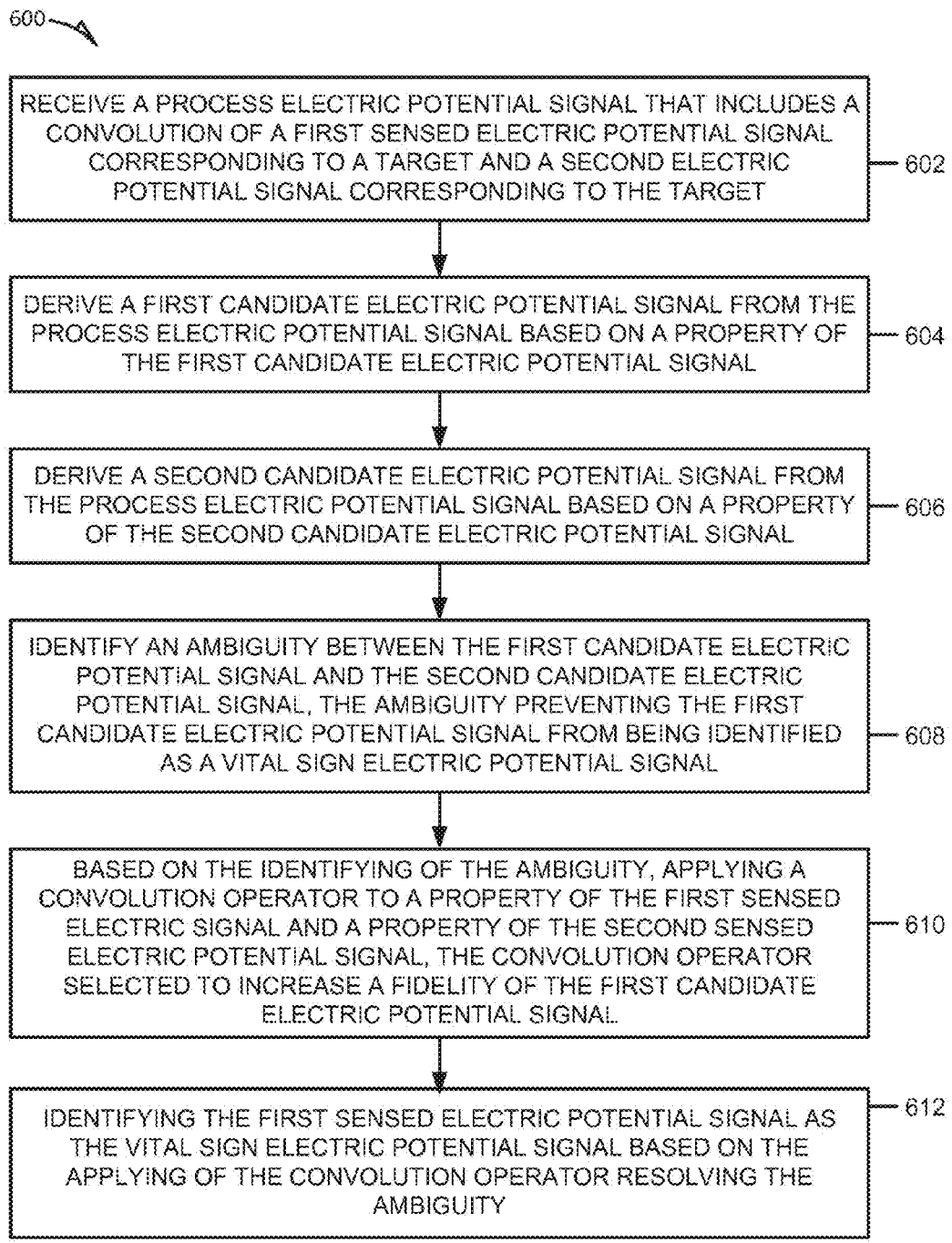
FIG. 6 is a flowchart depicting an example embodiment of a method of increasing fidelity of an electric potential signal.

FIG. 6 is a flowchart depicting an example method 600 of increasing a fidelity of an electric potential signal. Although FIG. 6 is described primarily in the context of detecting a fluctuation in an electric potential, the invention also applies to detecting a fluctuation in electric field, capacitance, dielectric constant, and/or any other suitable type of measurement. In various embodiments, the method 600 may be implemented by one or more of the modules of FIGS. 1-4. At operation 602, a signal is received. In certain instances, the received signal may be a conditioned signal 406 in the form of computer-readable data having a particular format suitable for processing by one or more microcontroller unit(s) of module 110. The received signal may include, for example, a convolution of data corresponding to at least (1) a first sensed electric potential signal corresponding to a target, and (2) a second electric potential signal corresponding to the target.

At operation 604, a first candidate electric potential signal is derived from the signal received at operation 602 based on a property of the first candidate electric potential signal. At operation 606, a second candidate electric potential signal is derived from the signal received at operation 602 based on a property of the second electrical potential signal. In various embodiments, the first candidate electric potential signal and the second candidate potential electric signal are derived based on an identification of a disturbance in an electrical field that is distinguished from background disturbances in an environment of the target. In various embodiments, the first candidate electric potential signal and the second candidate electric potential signal are derived based on one or more similarities of the properties of the candidate electric potential signals and the properties of previously-identified electric potential signals known to correspond to vital signs of a target.

At operation 608, a determination is made as to whether an ambiguity between the property of the first candidate electric potential signal and the property of the second candidate potential signal has prevented the first candidate electric potential signal from being identified as a vital sign electric potential signal. For example, an ambiguity may be identified based on the first candidate electric potential signal and the second candidate electric potential signal being distinguished from background disturbances in an environment of the target, but not being sufficiently distinguished from one another such that a correspondence between the first electric potential signal or the second electric potential signal to a particular vital sign (e.g., a heartbeat) of the target may be identified. That is, an ambiguity may exist when the system determines that there are multiple candidate electric potential signals being derived from the process electric potential signal that may correspond to a particular vital sign and the system does not have enough information (e.g., plotted data points) about the properties of the candidate electric potential signals to determine which of the candidate electric potential signals actually corresponds to the particular vital sign.

At operation 610, based on the determination of the ambiguity, a convolution operator is applied to the first sensed electric potential signal and a property of the second sensed electric potential signal. The convolution operator may be selected based on its likelihood of increasing a fidelity of the first candidate electric potential signal. At operation 612, the first candidate electric potential signal is identified as the vital sign electric potential signal based on the increasing of the fidelity resolving the ambiguity. For example, upon application of the convolution operator, the system may determine that the plotted data points corresponding to the first candidate potential electric potential signal have enough of a resemblance to predetermined patterns corresponding to the vital sign that the second candidate potential electric signal may now be ruled at as corresponding to the vital sign. Whether the first candidate electric potential signal has enough of a resemblance may be determined based on an analysis of similarities between the plotted data points corresponding to the first potential electric potential signal and the predetermined pattern transgressing a threshold. Or, whether the first candidate electric potential signal has enough of a resemblance may be determined based on an analysis of similarities between the plotted data points corresponding to the second potential signal and the predetermined pattern transgressing a threshold.

In other words, the system may resolve the ambiguity by determining that, after the application of the convolution operator, the first candidate electric potential signal is sufficiently similar to a predetermined pattern that the second candidate electric potential signal may be ruled out as corresponding to the vital sign. Or the system may resolve the ambiguity by determining that, after applying the convolution operator, the second candidate electric potential signal is sufficiently dissimilar to the predetermined pattern that the second candidate electric potential signal may be ruled out as corresponding to the vital sign.

In various embodiments, the ambiguity may be resolved by applying a convolution operator to the candidate electric potential signal and an additional candidate electric potential signal, the additional candidate electric potential signal being identified in an additional process electric potential signal derived from an additional electric field disturbance sensor. In other words, a candidate electric potential signal of a first process signal may be disambiguated from additional candidate electric potential signals of the first process signal by enhancing the candidate process electric signal based on electric potential signals in a second electric potential process signal that are identified (e.g., based on wavelet analysis) as corresponding to the candidate electric signal of the first electric potential process signal.

In various embodiments, the determination that a wave or signal in a process signal corresponds to a vital sign of the target includes comparing the waves detected by the sensors at a non-contact distance from the target with well-known waves, such as the P, Q, R, S, T waves of a heart muscle, as they would be detected by a sensor that is placed in contact with the target (e.g., by an ECG). In other words, signals sensed by an electric field disturbance sensor from a non-contact distance may have enough characteristics that are similar to well-known characteristics of different signals sensed by a different type of sensor (e.g., an ECG sensor) that a correspondence between the signals may be identified. That is, upon a threshold in similarity between the characteristics of the different waves of the different signal types being reached, the system 100 may identify a correspondence between the waves and thus identify a particular wave of a process signal as corresponding to a particular well-known vital sign signal.

In various embodiments, the active filtering method discussed above with respect to FIG. 6 may also be used to increase the fidelity of a candidate signal.

In various embodiments, a fidelity of a signal may be effected by a sensitivity setting controlled by the user of the system 100. The sensitivity setting, for example, may reduce the sensitivity of the electric field disturbance sensor(s) 106 at a particular frequency of main power (e.g., 50 Hz or 60 Hz). This changing of sensitivity, for example, may enable the user to control whether the system 100 is configured to more accurately monitor the whole body movements of the target or more accurately monitor particular vital signs (e.g., heart or eye movements of the target), such as in an environment in which a tradeoff must be made between the two types of monitoring.

Figure 7:
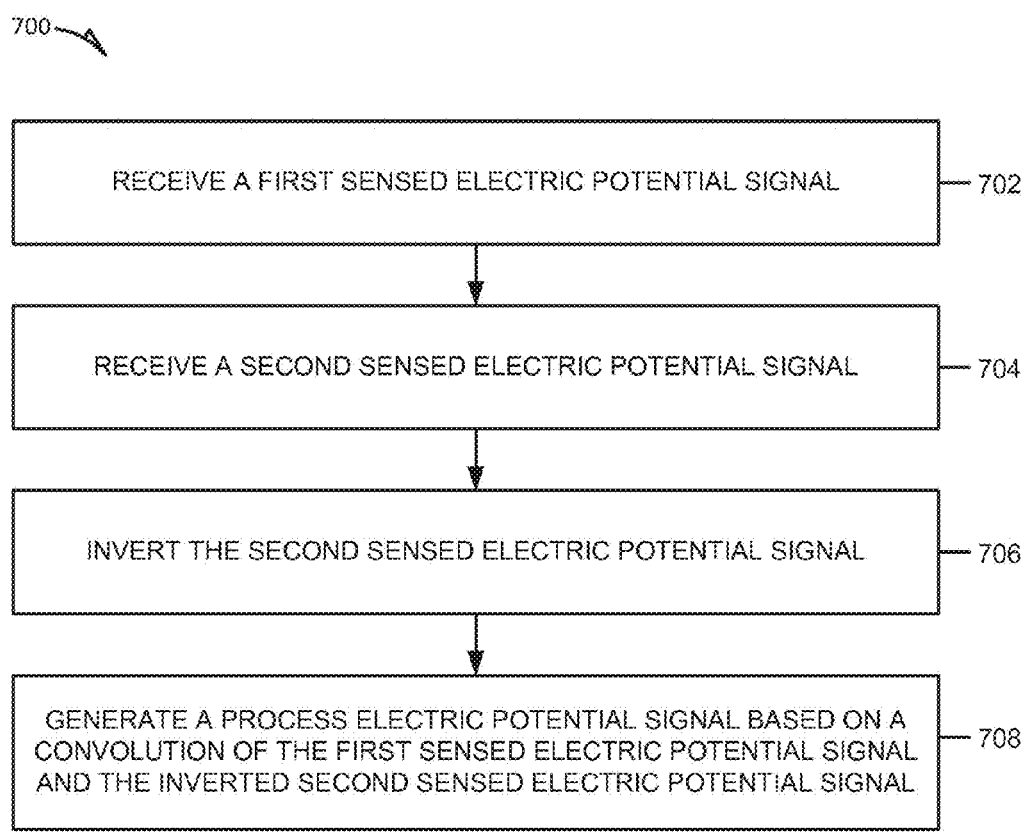
FIG. 7 is a flowchart depicting an example embodiment of a method of generating a process electric potential signal.

FIG. 7 is a flowchart depicting an example method 700 of generating a process electric potential signal. Although FIG. 7 is described primarily in the context of detecting a fluctuation in an electric potential, the invention also applies to detecting a fluctuation in electric field, capacitance, dielectric constant, and/or any other suitable type of measurement. In various embodiments, the method 700 may be implemented by one or more of the modules of FIGS. 1-4. At operation 702, a first sensed electric potential signal is received, the first sensed electric potential signal being derived from an electric field associated with a target. At operation 704, a second sensed electric potential signal is received, the second sensed electric potential signal being derived from an ambient electric field in a vicinity of the target. At operation 706, an inverted electric potential signal is generated from the second sensed electric potential signal. At operation 708, the process electric potential signal is generated based on a convolution of the inverted electric potential signal and the first sensed electric potential signal.

Figure 8:
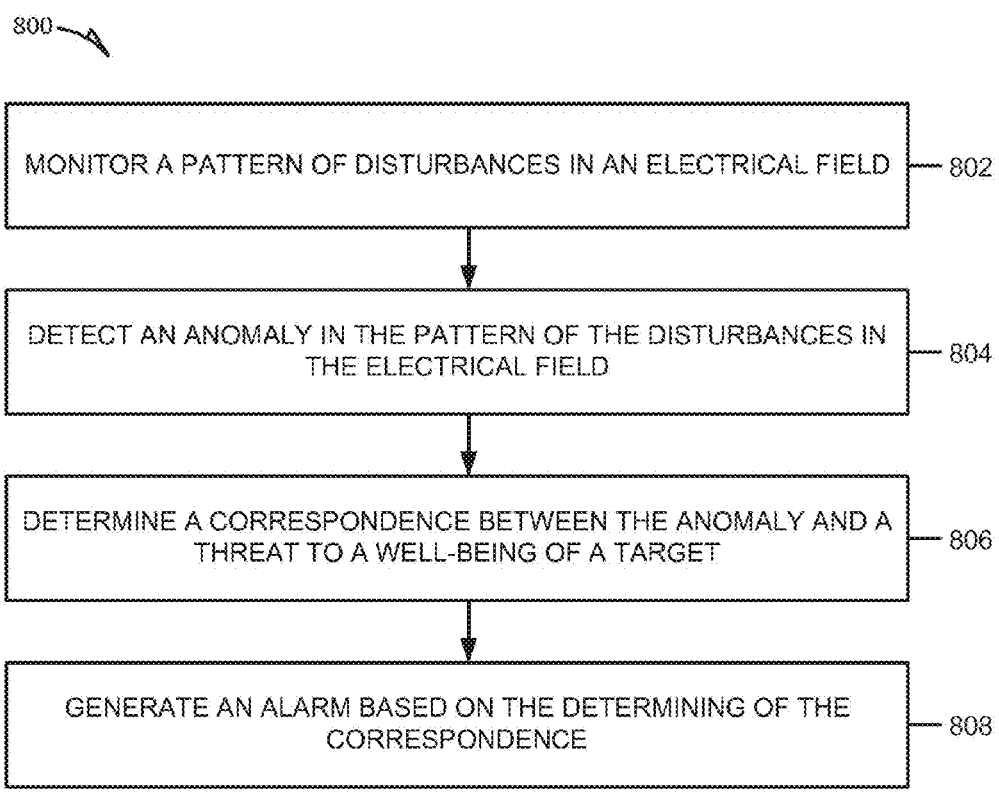
FIG. 8 is a flowchart depicting an example embodiment of a method of generating an alarm based on a detection of an anomaly in a pattern of disturbances in an electrical field.

FIG. 8 is a flowchart depicting an example method of generating an alarm based on a detection of an anomaly in a pattern of disturbances in an electrical field. Although FIG. 8 is described primarily in the context of detecting a fluctuation in an electric field, the invention also applies to detecting a fluctuation in electric potential, capacitance, dielectric constant, and/or any other suitable type of measurement. In various embodiments, the method 800 may be implemented by one or more of the modules of FIGS. 1-4. At operation 802, a pattern of disturbances in an electrical field is monitored. For example, the pattern of disturbances may correspond to a candidate electric potential signal that has been identified as a vital sign electric potential signal, as described in FIGS. 5-7. In various embodiments, the pattern of disturbances is detected in three dimensions (e.g., based on input from a plurality of sensors).

At operation 804, an anomaly in the pattern of the disturbances in the electrical field is detected. For example, an anomaly is detected in a pattern of disturbances corresponding to brain activity, heart activity, body movements, or eye (or eyelid) movements of the target. For example, the detection of the anomaly may be based on a comparison between the detected pattern and a reference pattern, as described above. In various embodiments, the reference pattern is a three-dimensional pattern.

At operation 806, a correspondence between the anomaly and a threat to the well-being of the target is determined. For example, it is determined that the activity level of the brain of the target (or a region of the brain) has dropped below a predetermined threshold value for a predetermined amount of time. Or it is determined that the heart rate of the individual has dropped below a predetermined threshold value (e.g., 30 beats per minute) for a predetermined amount of time (e.g., two minutes). Or it is determined that the body of the target has moved into a position that the body of the target has not been previously observed in. Or it is determined that the body of the target has not moved for a predetermined amount of time. Or it is determined that the eyelids of the target are moving at a slower-than-average rate for a predetermined amount of time.

At operation 808, an alarm is generated based on the determining of the correspondence between the anomaly and the threat to the well-being of the target. For example, the system emits a loud sound (e.g., like a fire alarm or digital clock alarm) or otherwise performs an action sufficient to notify a caretaker of the target of the detected emergency.

Figure 9:
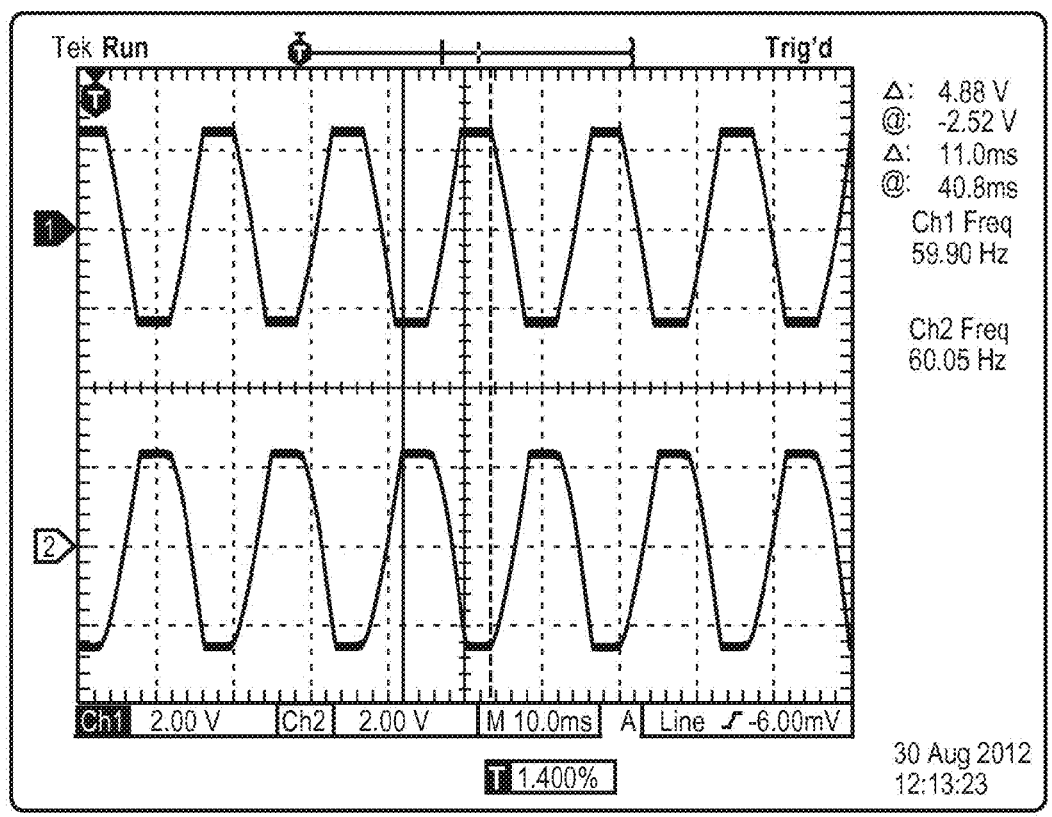
FIG. 9 is a chart depicting a plotting of data corresponding to signals received from one or more sensors of the system of FIG. 1 according to a particular embodiment.

FIG. 9 is a chart depicting a plotting of data corresponding to signals received from one or more sensors 106. In various embodiments, there may be high levels of background 60 Hz noise in an environment of a target. For example, high levels of background noise may be detected in a signal received from a single sensor 106 placed at a distance from a target. In various embodiments, the high levels of background 60 Hz noise may saturate amplifiers at gains that deliver signals corresponding to vital signs of the target. The plot at the top of the chart represents the background noise signal whereas the plot at the bottom of the chart represents a bandpass output signal.

Figure 10:
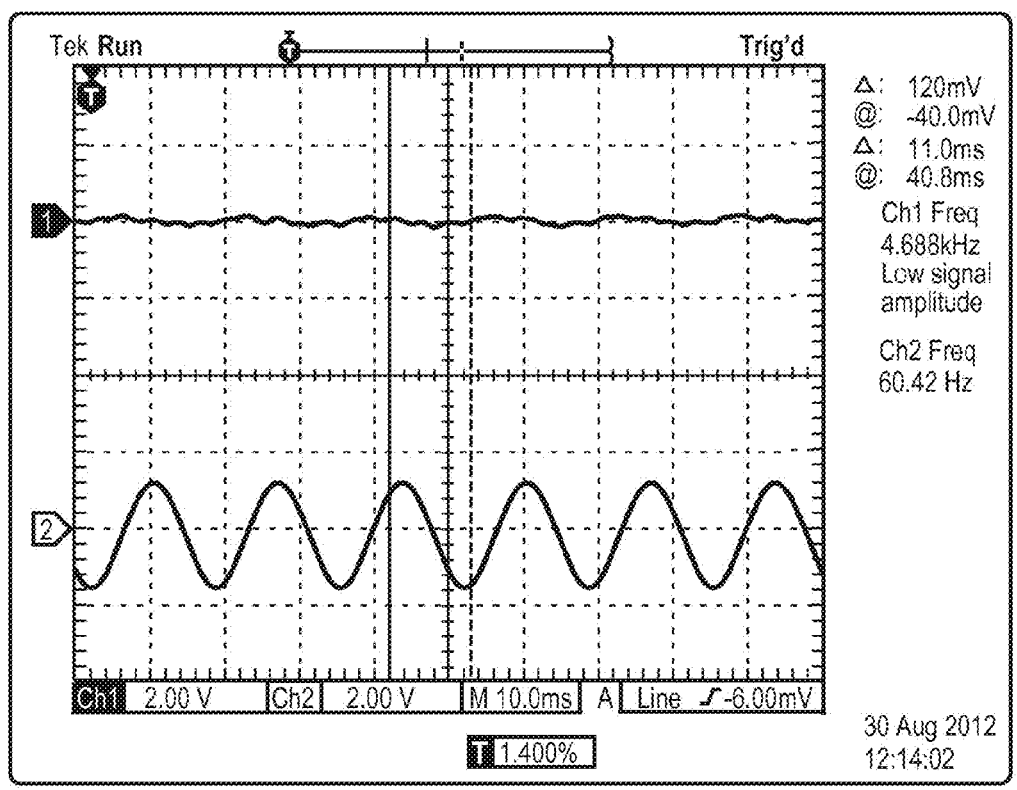
FIG. 10 is a chart depicting a plotting of data corresponding to signals received from one or more sensors of the system of FIG. 1, in which saturating noise has been suppressed according to a particular embodiment.

FIG. 10 is a chart depicting a plotting of data corresponding to signals received from one or more sensors 106 in which saturating noise has been suppressed. In various embodiments, such suppression may be accomplished with the use of a 60 Hz+ harmonics bandpass filter. For example, the 60 Hz+ harmonics bandpass filter may feed its output into the negative input of the sensor. As can be seen from a comparison of plotted data points in FIGS. 9 and 10, suppression of the saturating noise may also reduce the bandpass output.

In various embodiments, switched-capacitor filters may insert a small amount of phase lag in the feedback signal, which may limit the amount of suppression that can be achieved. However, the application of such filters may easily eliminate the amplifier-saturation problem. In various embodiments, an analog low-pass filter on the output may perform additional filtering.

Figure 11:
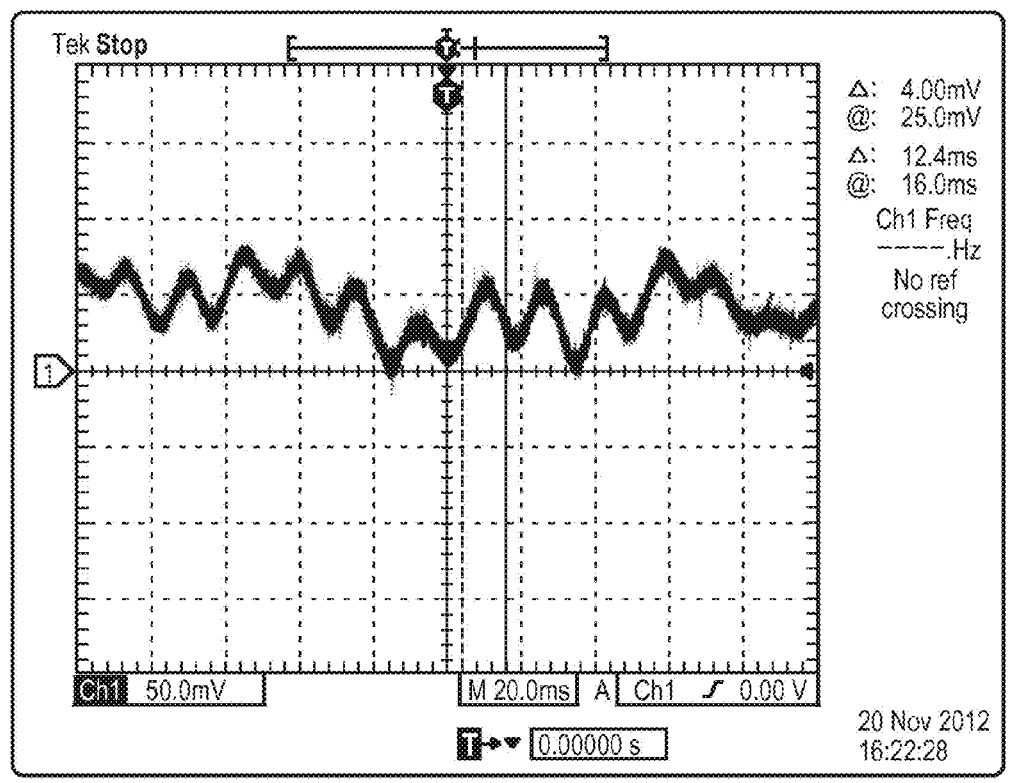
FIG. 11 is a chart depicting a plotting of data corresponding to signals received from one or more sensors of the system of FIG. 1, after the application of certain suppression and low-pass filtering according to a particular embodiment.

FIG. 11 is a chart depicting a plotting of data corresponding to signals received from one or more sensors after the application of suppression and low-pass filtering. In various embodiments, at a proper amplitude scale (e.g., 50 mV/div) and time scale (e.g., 20 ms/div), the residual 60 Hz noise may be viewed after suppression and low-pass filtering.

Figure 12:
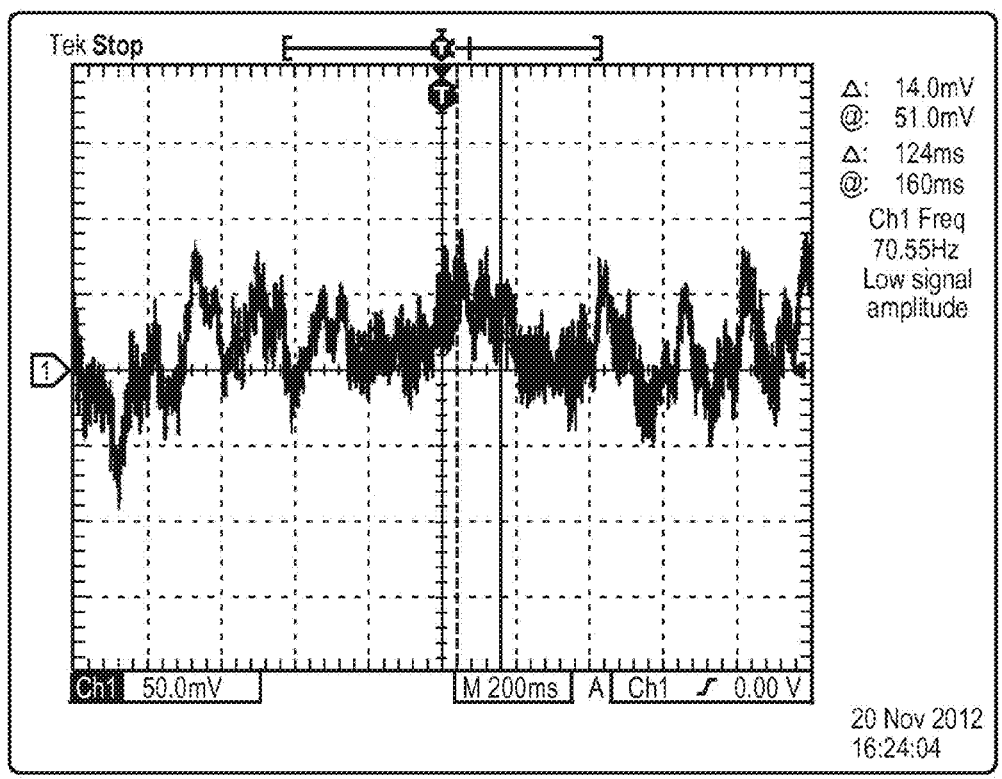
FIG. 12 is a chart depicting a plotting of data corresponding to signals received from one or more sensors after the application of more amplification, suppression, and/or low-pass filtering according to a particular embodiment.

FIG. 12 is a chart depicting a more amplified plotting of data corresponding to signals received from one or more sensors after the application of suppression and low-pass filtering. In various embodiments, signals corresponding to particular vital signs (e.g., EKG signals) may be detected at particular time scales (e.g., 200 ms/div). From a signal received from a sensor placed a few cm from a target, the chart depicts faint suggestions of the EKG complex occurring at 700-800 ms. Further processing, as described above, may discriminate this vital sign signal from background noise in the environment of the target.

Thus, a physio/motion sensor board may suppress the background interference at various frequencies (e.g., 60 Hz), which can saturate a sensitive high-impedance field detection amplifier. Further filtering in a DSP (e.g., a sharp LPF) may remove all noise at the frequency and above. A sharp HPF may remove body-motion artifacts. Then, vital sign signals may be detected at a non-contact range from the target. Use of multiple sensors (e.g., in a differential arrangement) may further improve the signal detection of the system (e.g., by increasing the fidelity of a vital sign signal).

Figure 13:
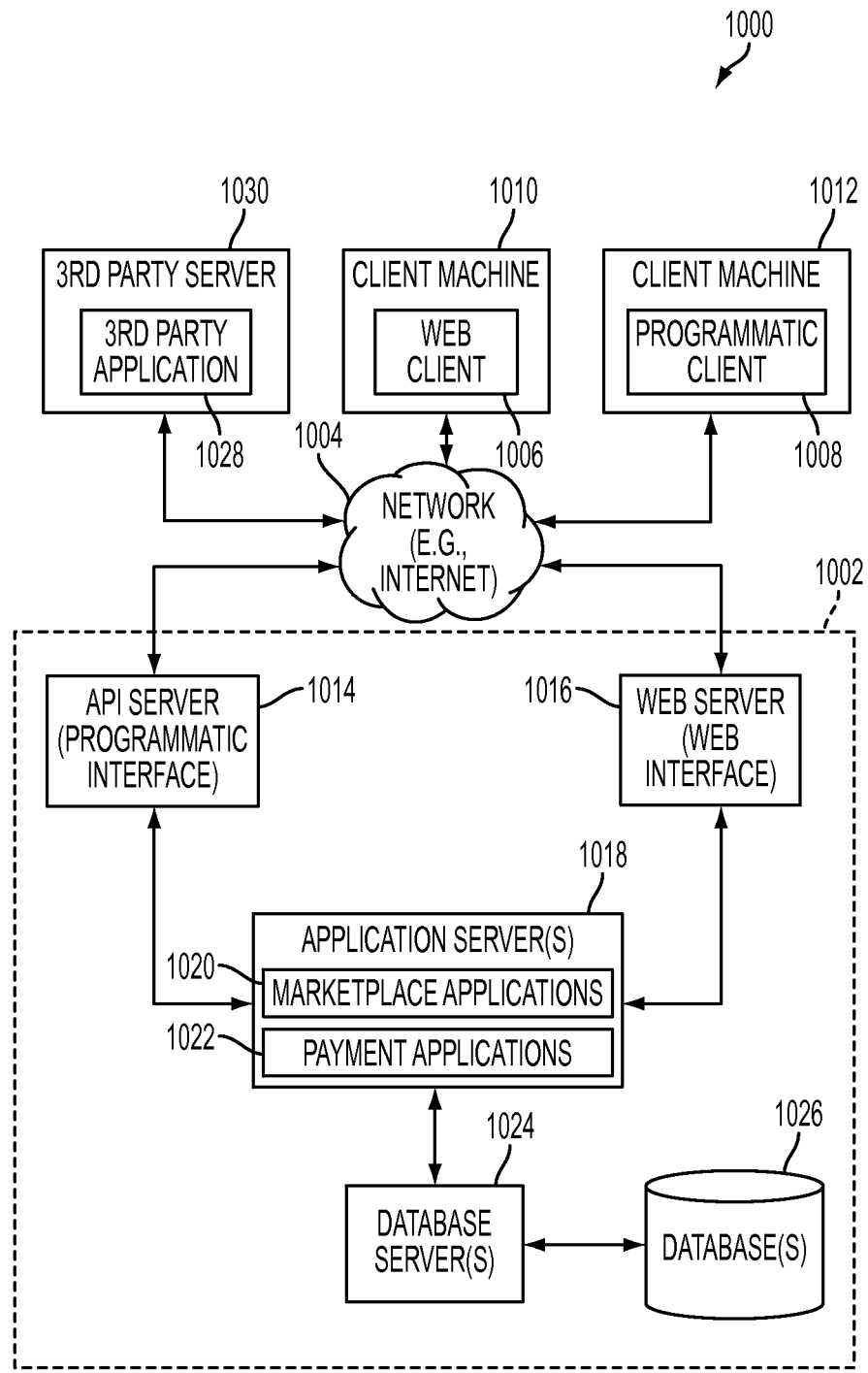
FIG. 13 is a network diagram depicting a client-server system within which various example embodiments may be deployed according to a particular embodiment.

FIG. 13 is a network diagram depicting a client-server system 1000, within which various example embodiments may be deployed. A networked system 1002, in the example form of a monitoring system, provides server-side functionality, via a network 1004 (e.g., the Internet or Wide Area Network (WAN)) to one or more clients. FIG. 13 illustrates, for example, a web client 1006 (e.g., a browser, such as the Internet Explorer browser developed by Microsoft Corporation of Redmond, Wash.) and a programmatic client 1008 executing on respective client machines 1010 and 1012. In various embodiments, the monitoring system 1002 may be embodied by the system 100 of FIG. 1.

Each of the one or more clients may include a software application module (e.g., a plug-in, add-in, or macro) that adds a specific service or feature to a larger system. The software application module may be separate from, though optionally may be integrated in whole or in part with, a user interface and functionality of a software application, such as a spreadsheet application. The software application may be a client software application executing on a client machine. The software application module may be optionally deployed in the same environment as the software application such that the software application module can be accessed from within the software application. The software application module may be optionally enabled or disabled within the environment (e.g., user interface) of the software application. The software application module may appear to be a part of the software application by, for example, providing user interface components or widgets (e.g., menus, toolbars, menu commands, toolbar commands, and so on) that can be enabled, disabled, added to, or removed from standard user interface components or widgets provided by the software application.

An API server 1014 and a web server 1016 are coupled to, and provide programmatic and web interfaces respectively to, one or more application servers 1018. The application servers 1018 host one or more marketplace applications 1020 and payment applications 1022. The application servers 1018 are, in turn, shown to be coupled to one or more database servers 1024 that facilitate access to one or more databases 1026 or NoSQL or non-relational data stores.

The applications 1020 may provide a number of functions and services to users that access the networked system 1002. While the applications 1020 are shown in FIG. 13 to both form part of the networked system 1002, in alternative embodiments, the applications 1020 may form part of a system that is separate and distinct from the networked system 1002. As an example, various modules depicted in FIG. 1 or FIG. 4 may be implemented as or included in applications 1020.

Further, while the system 1000 employs a client-server architecture, various embodiments are, of course, not limited to such an architecture, and could equally well find application in a distributed, or peer-to-peer, architecture system, for example. The various applications 1020 could also be implemented as standalone software programs, which do not necessarily have networking capabilities. Additionally, although FIG. 13 depicts machines 1030, 1010, and 1012 as being coupled to a single networked system 1002, it will be readily apparent to one skilled in the art that machines 1030, 1010, and 1012, as well as application 1028 and clients 1006 and 1008, may be coupled to multiple networked systems.

The web client 1006 accesses the various applications 1020 via the web interface supported by the web server 1016. Similarly, the programmatic client 1008 accesses the various services and functions provided by the applications 1020 via the programmatic interface provided by the API server 1014. The programmatic client 1008 may, for example, be an application executing on an iPhone that enables a user to control the system 100 of FIG. 1 remotely.

FIG. 13 also illustrates a third-party application 1028, executing on a third-party server machine 1030, as having programmatic access to the networked system 1002 via the programmatic interface provided by the API server 1014. For example, the third-party application 1028 may, utilizing information retrieved from the networked system 1002, support one or more features or functions on a website hosted by the third party. The third-party website may, for example, provide one or more functions that are supported by the relevant applications of the networked system 1002.

Certain embodiments are described herein as including logic or a number of components, modules, or mechanisms. Modules may constitute either software modules (e.g., code embodied on a non-transitory machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the network 104) and via one or more appropriate interfaces (e.g., APIs).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a non-transitory machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., an FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 14:
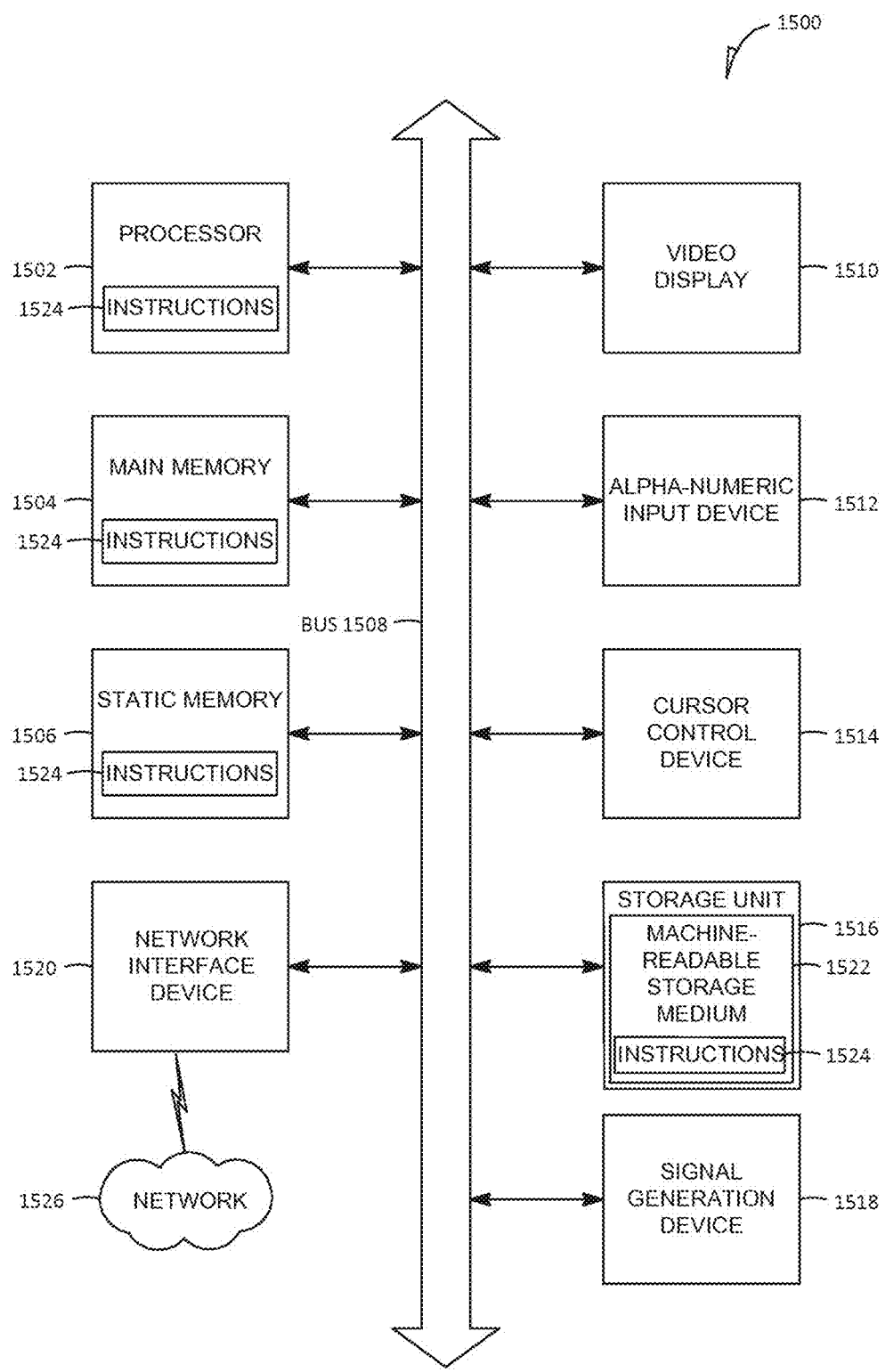
FIG. 14 is a block diagram of a machine in the example form of a computer system within which instructions for causing the machine to perform any one or more of the methodologies discussed herein may be executed.

FIG. 14 is a block diagram of a machine in the example form of a computer system 1500 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1500 includes a processor 1502 (e.g., a central processing unit (CPU), a graphics processing unit (GPU) or both), a main memory 1504 and a static memory 1506, which communicate with each other via a bus 1508. The computer system 1500 may further include a video display unit 1510 (e.g., a liquid crystal display (LCD) or a cathode ray tube (CRT)). The computer system 1500 also includes an alphanumeric input device 1512 (e.g., a keyboard), a user interface (UI) navigation (or cursor control) device 1514 (e.g., a mouse), a storage (e.g., disk drive) unit 1516, a signal generation device 1518 (e.g., a speaker) and a network interface device 1520.

The disk drive unit 1516 includes a non-transitory machine-readable medium 1522 on which is stored one or more sets of data structures and instructions (e.g., software) embodying or utilized by any one or more of the methodologies or functions described herein. The instructions 1524 may also reside, completely or at least partially, within the main memory 1504 and/or within the processor 1502 during execution thereof by the computer system 1500, the main memory 1504 and the processor 1502 also constituting non-transitory machine-readable media. The instructions 1524 may also reside, completely or at least partially, within the static memory 1506.

While the non-transitory machine-readable medium 1522 is shown in an example embodiment to be a single medium, the term "non-transitory machine-readable medium" may include a single medium or multiple media (e.g., a centralized or distributed database, and/or associated caches and servers) that store the one or more instructions 1524 or data structures. The term "non-transitory machine-readable medium" shall also be taken to include any tangible medium that is capable of storing, encoding or carrying instructions for execution by the machine and that cause the machine to perform any one or more of the methodologies of the present embodiments, or that is capable of storing, encoding or carrying data structures utilized by or associated with such instructions. The term "non-transitory machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-only Memory (EPROM), Electrically Erasable Programmable Read-Only Memory (EEPROM), and flash memory devices; magnetic disks such as internal hard disks and removable disks; magneto-optical disks; and compact disc-read-only memory (CD-ROM) and digital versatile disc (or digital video disc) read-only memory (DVD-ROM) disks.

The instructions 1524 may further be transmitted or received over a communications network 1526 using a transmission medium. The instructions 1524 may be transmitted using the network interface device 1520 and any one of a number of well-known transfer protocols (e.g., HTTP). Examples of communication networks include a LAN, a WAN, the Internet, mobile telephone networks, POTS networks, and wireless data networks (e.g., WiFi and WiMax networks). The term "transmission medium" shall be taken to include any intangible medium capable of storing, encoding or carrying instructions for execution by the machine, and includes digital or analog communications signals or other intangible media to facilitate communication of such software. In various embodiments, the network 1526 may correspond to the network 1004.

Certain embodiments disclosed herein may be integrated in whole or in part with each other. For example, the system 100 of FIG. 1 may be an example embodiment of, or form at least a portion of, the computer system 1500 of FIG. 14, and vice versa.

FIGS. 1-14 have been described primarily in the context of monitoring systems that use electric potential sensors or electric field disturbance sensors to monitor vital signs based on sensed changes to an electric field or electric potential. However, the invention is not limited to using those particular types of sensors to sense changes to an electric field or electric potential. In other embodiments, the invention as described above in connection with FIGS. 1-14 can also apply to sensors that monitor vital signs based on sensed changes in capacitance, dielectric constant, and/or any other suitable type of measurement.

One or more sensors can be used to monitor a target. Each sensor can include a capacitor, an oscillator, and a frequency-to-voltage converter. Alternatively, multiple sensors can share the same oscillator and/or frequency-to-voltage converter. Any other suitable additional or alternative components can also be included as part of, or external to, the sensor in order to augment the data being collected on the target. For instance, a system monitoring a target lying on a bed may also include one or more pressure gauges to verify when the target is actually lying on the bed before activating the sensors to collect data. Similarly, the number of sensors used in the system can vary depending upon the amount and type of data to be collected. In some embodiments, one sensor may be used. In other embodiments, two or more sensors may be used to get two, three, or other multi-dimensional data or directional data.

The sensors can be placed in any suitable position and/or distance relative to the target. In some embodiments, the sensor can be positioned near the target and/or part(s) with the target (e.g., for a human, different body parts) being monitored. In some embodiments, the sensors can be positioned around the target to detect two, three, or other multi-dimensional data on the target. The sensors can be positioned at the same distances, different distances, or some combination thereof, relative to the other sensors. In some embodiments, the sensors can be positioned near each other in the same space to detect directional movement of the target. In some embodiments, the sensors can be positioned at the same or different distances from the target. For example, the sensors can be located any suitable distance or distances from the target (e.g., 1-10 ft., 15 ft., 20 ft., 25 ft., 30 ft., 35 ft., 40 ft., 45 ft., 50 ft., 100 ft.).

Figure 15:
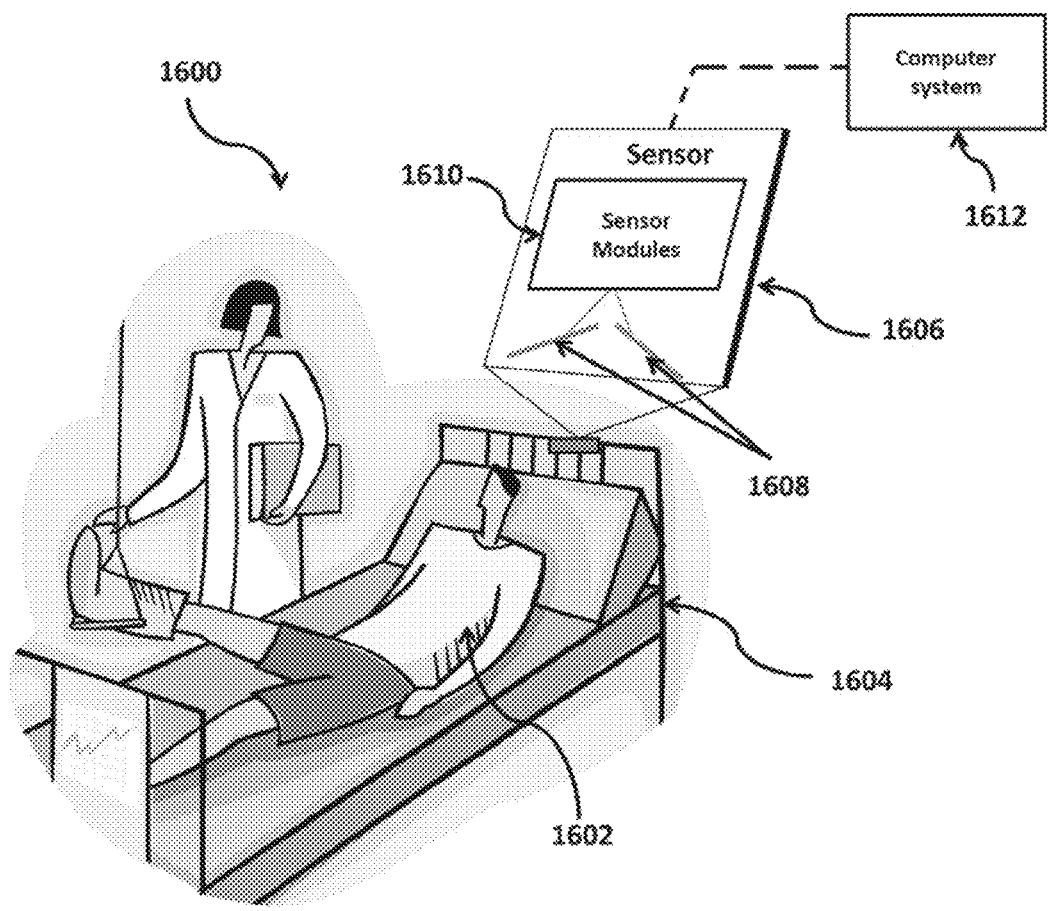
FIG. 15 is a diagram showing a monitoring system with a contact-less sensor for monitoring changes in the capacitance and/or dielectric constant of a target according to another embodiment.

FIG. 15 is a diagram of a monitoring system 1600 with a contact-less sensor for monitoring changes in the capacitance and/or dielectric constant of a target according to an embodiment. A human target 1602 is lying on a bed 1604. A contact-less sensor 1606 can be placed near, but not on, the target, for example, on the target's bed 1604. FIG. 15 shows that the target is human and a sensor 1606 is placed near the head of the target's bed 1604. However, the target can be any suitable target in any suitable location that can affect a change in capacitance or dielectric constant as detected by the sensor. In addition, more than one sensor can be used and placed in any other suitable position near the target. Furthermore, the sensor can be used for any suitable purpose and to measure any suitable measurement. In one embodiment, for example, a target may be a patient undergoing a particular medical observation.

The sensor 1606 can detect changes in the capacitance and/or dielectric constant of the target or part of the target being monitored. The sensor 1606 can include a capacitor 1608 and other sensor modules 1610, the output of which can be sent to a computer system 1612 for further analysis and output. In one embodiment, the capacitor 1608 can include two capacitive plates. The two capacitive plates can be arranged in close physical proximity to, and opened in the direction of, the target or the part of the target being monitored. The sensor modules 1610 can include any suitable components including, for example, an oscillator and a frequency-to-voltage converter. The one or more sensors 1606, using the capacitor 1608 and other sensor modules 1610, can detect and communicate signals corresponding to changes in capacitance and/or dielectric constant to the computer system 1612, which analyzes the signal and provides an output as described in connection with FIG. 16.

Figure 16:
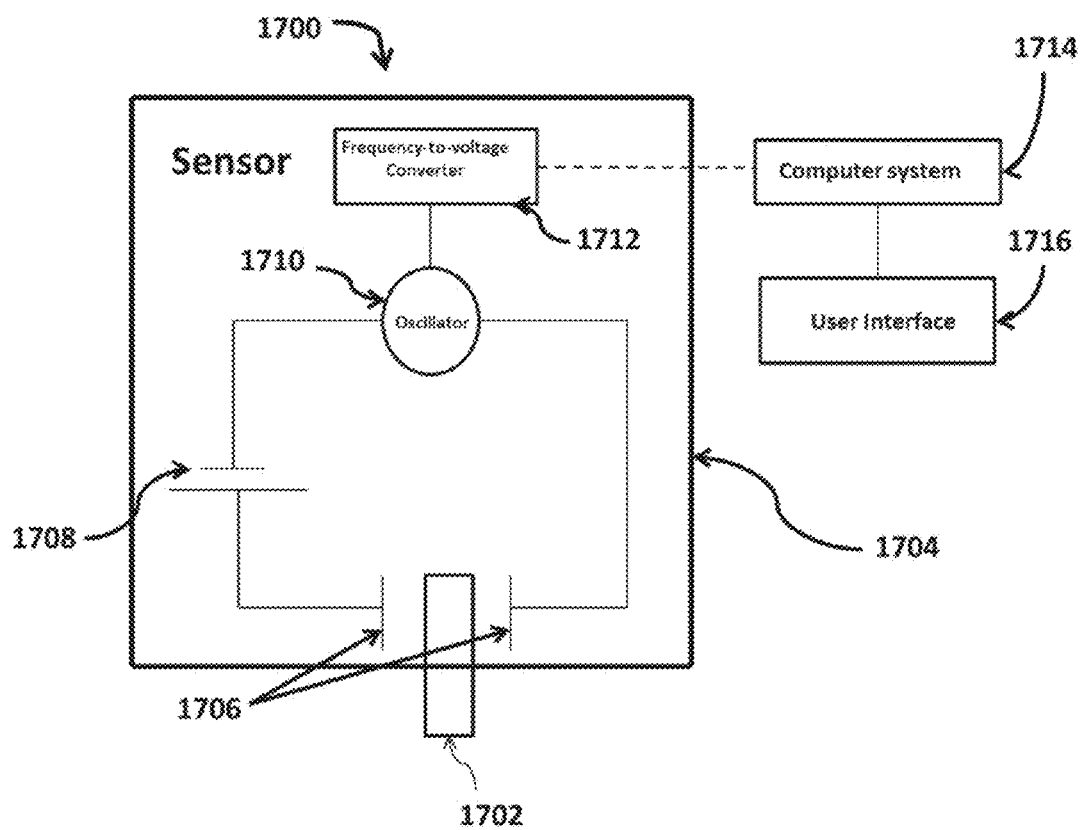
FIG. 16 is a block diagram of a monitoring system with a contact-less sensor for monitoring changes in the capacitance and/or dielectric constant of the target according to another embodiment.

FIG. 16 is a block diagram of a monitoring system 1700 with a contact-less sensor for monitoring changes in the capacitance and/or dielectric constant of the target according to an embodiment. The illustrated embodiment includes a target 1702, a sensor 1704, a computer system 1714, and a user-interface 1716. However, the instant invention is not limited by these exemplary modules; any suitable modules may be used including, for example, additional or alternative modules. As used herein, the term module generally refers to any suitable combination of hardware, software, or firmware configured to facilitate the monitoring of capacitance and/or dielectric constant.

As shown in FIG. 16, the sensor 1704 includes a capacitor 1706, a voltage source 1708, an oscillator 1710 and a frequency-to-voltage converter 1712. The target 1702 is positioned in the field of a capacitor 1706, such that the target is not in contact with the plates of the capacitor. Although FIG. 16 shows capacitor 1706 as having parallel plates, the plates can be oriented at any suitable angle (e.g., from 0°-180°). The capacitor 1706 may be charged by one or more power supplies 1708, for example, to receive power from any suitable power source (e.g., a battery, an alternating current (AC) line). The power supply 1708 may also supply power to various other modules of the monitoring system (e.g., at specific voltages required by the other modules). For example, power supply 1708 may include a power supply having a three Volt (3V) or similar input. Furthermore, power supply 1708 may include a buck-boost converter configured to minimized losses from input voltage to source load.

An oscillator 1710 may detect the frequency of the changes in the capacitance and/or dielectric constant of the target. The oscillator can be any type of oscillator that is suitable for detecting the frequency of change in capacitance and/or dielectric constant of the target. It may be configured, for example, to detect fluctuation in dielectric constant and, in response to, generate a detection signal corresponding to the detected fluctuation. The oscillator 1710 is connected to a frequency-to-voltage converter 1712. The frequency-to-voltage converter 1712 converts the input frequency into a proportional voltage, which is generally linear to the input frequency. It may also act as an analog-to-digital converter. In one embodiment, the frequency-to-voltage converter 1712 may generate a voltage-time graph of the received signal. Higher full-scale frequencies or longer count intervals can be used for higher resolution conversions. For example, the linearity error can be 0.001%, to 0.1% depending upon the frequency.

The computer system 1714 may receive data from one or more sensors 1704, analyze it and communicate this data through a user interface 1716. The computer system 1714 may include one or more processors or microcontrollers coupled to memory configured to process signals received from one or more other modules. For example, it may receive a signal from the frequency-to-voltage convertor 1712 and determine the presence of a pattern and whether there is a deviation from a normal pattern. It may also receive communications from the user-interface 1716 and appropriately control the sensitivity and frequency of the signal received. In a particular embodiment, the computer system 1714 is communicatively coupled to the sensor 1704, in particular the frequency-to-voltage converter 1712, and the user interface 1716, wirelessly or by wired communication.

The user interface 1716 provides an interface between the various modules collecting and analyzing data about the target and the user. In certain embodiments, the user interface 1716 may receive communications from the computer system and translate them into a format that is appropriate for the particular user interface 1716. The user interface 1716 may include one or more sensitivity controls (e.g., dials) configured to enable a user to control the sensitivity of the signals received either singularly or collectively (e.g., at particular frequencies). It may also permit users to program input signal range and full-scale output range. The user interface 1716 may be configured for a user to input data such as a patient's medical history, personal information, or any other suitable information. In certain embodiments, the user interface may alert the user by triggering an alarm when the signal deviates from a pre-determined threshold or pattern. The user interface 1716 may include a visual graphics display and an input device such as, for example, a keypad, keyboard, mouse, touchpad, trackpad or joystick. In some embodiments, the visual graphics display of the user interface may be a touch-sensitive monitor. It may also be compatible for communications over SPI, USB, USART, RS-232, BLUETOOTH, ZIGBEE, Ethernet, etc. In some embodiments, the user interface 1716 may be built into the computer system 1714. In some embodiments, the user interface 1716 may be configured to operate on personal devices such as personal computers, tablets, smartphones, or other mobile devices.

In some embodiments, the user interface 1716 may be part of the computer system 1714. In some embodiments, modules 1712, 1714 and 1716 may, together or separately, condition the received signal, and communicate a corresponding conditioned signal as an output. In particular embodiments, the signal conditioning may include filtration, amplification, conversion (e.g., inversion or analog-to-digital conversion), any combination thereof, or any other suitable signal conditioning that effects a transformation of the signal. In some embodiments, the signals are communicated to the user in easily readable formats such as digital values or graphs.

FIG. 17 shows examples of different orientations of the capacitive plates of the sensors with respect to the target. FIG. 17A shows capacitive plates 1804 at an angle of 180° with respect to each other. The target 1802 is preferably positioned within the electric field 1806 of the capacitor. In FIG. 17B the capacitive plates 1904 are at an angle less than 180 with respect to each other. The target 1902 is preferably positioned within the electric field 1906 of the capacitor. In FIG. 17C, the capacitive plates are at an angle of 0° with respect to each other (e.g., parallel). The target 2002 is preferably positioned within the electric field 2006. The two capacitive plates can be floating plates that can be arranged at any suitable angle between (and including) 0° to 180° (e.g., 45°, 90°, 135°, 180°) as long as the target is positioned within the electric field of the capacitor.

This invention may be used in various settings and to monitor various targets. The invention can be used, for example, in health care facilities, homes, offices, vehicles, gyms, sports facilities, or any other suitable location. The signals generated may also be used in identifying targets in high-security areas, with each target generating a unique signal pattern. Examples of targets that can be monitored by this system may include babies, children, teens, adults, senior citizens, and/or animals. Any of these targets can be monitored in any suitable setting, including, for example, babies in neonatal settings; babies in a crib; babies and/or children at high risk of sudden infant death syndrome (SIDS) or other health conditions; individuals prone to seizures, sleep disorders (e.g., sleep walking, sleep apnea, etc.), cardiovascular disease, or other medical condition;

individuals in a hospital setting; senior citizens or ill individuals in a care facility; and individuals in a gym or sports facility. Some targets may use the invention as a fitness monitor worn on or near the body of the target or placed directly into a smartphone. Sensors may also be incorporated into any suitable clothing or device that can be strapped to an individual to monitor the individual during a workout or sporting activity.

In some embodiments, the monitoring system may be used to alert various parties to a dangerous condition that is present with a given target. For example, the system could sound an alarm and/or alert the parents if the system detects that a child stopped breathing for a certain number of seconds. As another example, the system could sound an alarm or alert caregivers or emergency personnel if the system detects that a senior citizen had a heart attack, stopped breathing for a certain number of seconds, had not gotten out of bed beyond a certain number of days, or any other detected condition. As yet another example, the system could sound an alarm if the system detects that an individual who suffers from sleepwalking has left his/her bed or his/her room.

In some embodiments, the monitoring system may be placed in a child's crib and can alert the parents when the system detects any changes in their child's breathing, heart rate or movement. Existing products rely solely on the child's movement, or lack thereof, to alert parents of a problem. This system could identify a problem much earlier by detecting when the child's breathing or heart rate has changed. If a sibling or a pet gets into a crib, the system may immediately detect a second heart beat and sound an appropriate alarm.

In some embodiments, the monitoring system may also be used as a proximity sensor. For example, the system may detect when a target has left or entered a particular place, such as a bed, desk or room. A system using multiple sensors can track the movement of the target within a monitored zone. This may be useful, for example, in monitoring children, patients or senior citizens.

In some embodiments, the monitoring system may monitor a target over a period of time to detect any changes or abnormalities in that target. For example, the system may be used to monitor the effects of medication or some therapeutic or non-therapeutic intervention. The system may monitor the target for both known and unknown effects of an intervention, such as an increase in heart rate, breathing, impact on sleep, etc. In some embodiments, the system may be used to monitor changes in specific organs or body parts of the target. Each organ or body part may generate unique signal patterns, which may be monitored to identify changes with them. By identifying signals associated with different body parts, the system may also enable gesture recognition capabilities.

In some embodiments, the system may store data collected from various targets. The stored data may then be analyzed to better predict various health issues. For example, some studies have found that there may be a link between the amount of sleep and the risk of heart attack. The system could be used to find similar links between diseases or conditions with sleep or other activity or inactivity of the target. In other words, the system could be used as a prognostic and diagnostic tool as well.

In some embodiments, the monitoring system may identify a target with a signal that has a unique biological "fingerprint" to determine security access. For example, a person trying to get into a secured area through an entry door may be denied access by the system if it determines, based on his or her unique signal pattern, that he/she is not authorized to have access. The system may also be used to monitor access to secured machines, mobile devices, systems or databases.

In some embodiments, the invention may apply to an automotive setting. As discussed earlier, the system may be used to monitor the health of a vehicle's occupants, especially the driver. For example, the system may collect signals pertaining to the heart rate (and respiration) of the driver and calculate heart rate variability. Based on a pattern of heart rate and its variability, the system can determine whether the driver is feeling drowsy or experiencing some other medical condition, and then warn the driver to take corrective action or modify various settings on the vehicle. The system may also be used to monitor the positioning of an occupant of the vehicle. By communicating this information to a vehicle's air-bag control system, the system may aid in making the determination on when/if airbags should be deployed and to what "stage" they should be deployed. Another example of the use of the system in a vehicle would be to monitor for occupants left behind (e.g., parents accidentally leaving their children in the car) and then take corrective action. The uses of this system are not limited to the drivers of a vehicle but to all its occupants as well as occupants of all types of vehicles such as buses, trucks, cars, airplanes, ships, etc.

In the specification, the singular forms also include the plural, unless the context clearly dictates otherwise. As used herein, unless specifically indicated otherwise, the word "or" is used in the inclusive sense of "and/or" and not the exclusive sense of "either/or." Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously. Unless defined otherwise, all technical and scientific terms used herein have the same meaning as commonly understood by one of ordinary skill in the art to which this invention belongs.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based, may readily be utilized as a basis for the designing of other structures, systems, methods and media for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

Although an embodiment has been described with reference to specific example embodiments, it will be evident that various modifications and changes may be made to these embodiments without departing from the broader spirit and scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A method comprising:
electronically receiving, by a computer system, data representing a signal generated at least in part by one or more sensors detecting a change in capacitance or dielectric constant of a target that is physically spaced apart from the one or more sensors, wherein each of the one or more sensors does not move with the target;
identifying, using the computer system and based at least in part on the data electronically received by the computer system, a recurring pattern in the data; and
determining, using the computer system and based at least in part on the data electronically received by the computer system, whether a deviation from the recurring pattern transgresses a threshold, the deviation comprising a subset of the data electronically received by the computer system.

2. The method of claim 1, further comprising determining the threshold based at least in part on the recurring pattern, such that the threshold corresponds to a threat to the well-being of the target.

3. The method of claim 1, wherein the recurring pattern is based at least in part on an estimated position of the target in three-dimensional space.

4. The method of claim 1, wherein the recurring pattern corresponds to a vital sign of the target.

5. The method of claim 1, wherein the recurring pattern corresponds to a movement of the target and wherein the deviation is caused at least in part by a particular movement of the target.

6. The method of claim 1, wherein the recurring pattern corresponds to a recurring muscular movement of the target.

7. The method of claim 1, further comprising generating an alarm based at least in part on a determination that the deviation from the recurring pattern transgresses the threshold, the alarm indicating a threat to the well-being of the target.

8. A system comprising:
a memory; and
one or more processors coupled to the memory, the one or more processors configured to, based on instructions contained in the memory:
electronically receive data representing a signal generated at least in part by one or more sensors detecting a change in capacitance or dielectric constant of a target that is physically spaced apart from the one or more sensors, wherein each of the one or more sensors does not move with the target,
identify, based at least in part on the data electronically received, a recurring pattern in the data representing a signal, and
determine, based at least in part on the data electronically received, whether a deviation from the recurring pattern transgresses a threshold, the deviation comprising a subset of the data electronically received.

9. The system of claim 8, wherein each sensor further comprises:
a capacitor having two plates arranged to detect the capacitance or the dielectric constant of the target;
an oscillator, coupled to the capacitor, configured to detect the change of the capacitance or the dielectric constant of the target; and
a frequency-to-voltage converter, coupled to the oscillator, configured to convert the change in the capacitance or the dielectric constant of the target from a frequency to a voltage.

10. The system of claim 9, wherein the target is placed in the electric field of the capacitor's two plates.

11. The system of claim 9, wherein the capacitor's two plates are arranged at an angle between 0° to 180° with respect to each other.

12. The system of claim 9, wherein the capacitor's two plates are arranged at an angle of approximately 180° with respect to each other.

13. The system of claim 8, wherein the one or more processors are configured to, based on instructions contained in the memory, determine the threshold based at least in part on the recurring pattern, such that the threshold corresponds to a threat to the well-being of the target.

14. The system of claim 8, wherein the recurring pattern is based at least in part on an estimated position of the target in three-dimensional space.

15. The system of claim 8, wherein the recurring pattern corresponds to a vital sign of the target.

16. The system of claim 8, wherein the recurring pattern corresponds to a movement of the target and wherein the deviation is caused at least in part by a particular movement of the target.

17. The system of claim 8, wherein the recurring pattern corresponds to a recurring muscular movement of the target.

18. The system of claim 8, wherein the one or more processors are further configured to, based on instructions contained in the memory, generate an alarm based at least in part on a determination that the deviation from the recurring pattern transgresses the threshold, the alarm indicating a threat to the well-being of the target.

19. A non-transitory machine-readable medium storing a set of instructions that, when executed by at least one processor, causes the at least one processor to perform operations comprising:
  electronically receiving data representing a signal generated at least in part by one or more sensors detecting a change in capacitance or dielectric constant of a target that is physically spaced apart from the one or more sensors, wherein each of the one or more sensors does not move with the target;
  identifying, based at least in part on the data electronically received, a recurring pattern in the data representing a signal; and
  determining, based at least in part on the data electronically received, whether a deviation from the recurring pattern transgresses a threshold, the deviation comprising a subset of the data electronically received.

20. A system comprising:
  one or more sensors configured to detect a change in capacitance or dielectric constant of a target that is physically spaced apart from the one or more sensors, each sensor does not move with the target and comprising:
    a capacitor having two plates arranged to detect the capacitance or the dielectric constant of the target,
    an oscillator, coupled to the capacitor, configured to detect the change of the capacitance or the dielectric constant of the target, and
    a frequency-to-voltage converter, coupled to the oscillator, configured to convert the change in the capacitance or the dielectric constant of the target from a frequency to a voltage; and
  a computer having a memory and one or more processors coupled to the memory, the one or more processors configured to, based on instructions contained in the memory:
    electronically receive data representing a signal generated at least in part by the one or more sensors,
    identify, based at least in part on the data electronically received, a recurring pattern in the data representing a signal, and
    determine, based at least in part on the data electronically received, whether a deviation from the recurring pattern transgresses a threshold, the deviation comprising a subset of the data electronically received.

* * * * *